United States Patent
Cao et al.

(10) Patent No.: US 9,675,261 B2
(45) Date of Patent: Jun. 13, 2017

(54) ATRIAL ARRHYTHMIA EPISODE DETECTION IN A CARDIAC MEDICAL DEVICE

(71) Applicant: Medtronic, Inc., Minneapolis, MN (US)

(72) Inventors: Jian Cao, Shoreview, MN (US); Paul J. Degroot, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/004,202

(22) Filed: Jan. 22, 2016

(65) Prior Publication Data
US 2016/0213270 A1   Jul. 28, 2016

Related U.S. Application Data

(60) Provisional application No. 62/107,138, filed on Jan. 23, 2015.

(51) Int. Cl.
*A61B 5/04* (2006.01)
*A61B 5/00* (2006.01)
(Continued)

(52) U.S. Cl.
CPC .......... *A61B 5/04012* (2013.01); *A61B 5/046* (2013.01); *A61B 5/0464* (2013.01);
(Continued)

(58) Field of Classification Search
CPC .. A61N 1/3624; A61B 5/04012; A61B 5/046; A61B 5/0464; A61B 5/045525; A61B 5/0456; A61B 5/686
See application file for complete search history.

(56) References Cited

U.S. PATENT DOCUMENTS 4,226,245 A   10/1980   Bennett, Jr.
4,374,382 A    2/1983   Markowitz
(Continued)

FOREIGN PATENT DOCUMENTS

EP   2572634   3/2013
WO   9809241   3/1998
(Continued)

OTHER PUBLICATIONS

Couceiro et al., "Detection of Atrial Fibrillation Using Model-Based ECG Analysis", 19th International Conference on Pattern Recognition, Dec. 2008, 5 pages.
(Continued)

*Primary Examiner* — Robert N Wieland

(57) ABSTRACT

A method and medical device for detecting a cardiac event that includes sensing a cardiac signal, identifying R-waves in the cardiac signal attendant ventricular depolarizations, determining RR-intervals between successive R-waves in response to the sensed cardiac signal, detecting an atrial tachyarrhythmia based on an analysis of the RR-intervals, iteratively sensing groups of a predetermined number of P-waves attendant atrial depolarizations in response to detecting the atrial tachyarrhythmia, and confirming the atrial tachyarrhythmia based on an analysis of the iteratively sensed groups of P-waves.

23 Claims, 15 Drawing Sheets

(51) Int. Cl.
  *A61B 5/0452*   (2006.01)
  *A61B 5/046*    (2006.01)
  *A61B 5/0464*   (2006.01)
  *A61N 1/362*    (2006.01)
  *A61N 1/37*     (2006.01)
  *A61N 1/39*     (2006.01)

(52) U.S. Cl.
  CPC .......... *A61B 5/04525* (2013.01); *A61B 5/686* (2013.01); *A61B 5/7264* (2013.01); *A61B 5/7282* (2013.01); *A61N 1/3624* (2013.01); *A61N 1/3702* (2013.01); *A61N 1/3987* (2013.01); *A61N 1/3956* (2013.01)

(56) References Cited

U.S. PATENT DOCUMENTS

| | | |
|---|---|---|
| 4,721,114 A | 1/1988 | DuFault et al. |
| 5,117,824 A | 6/1992 | Keimel et al. |
| 5,193,535 A | 3/1993 | Bardy et al. |
| 5,292,338 A | 3/1994 | Bardy |
| 5,312,445 A | 5/1994 | Nappholz et al. |
| 5,334,221 A | 8/1994 | Bardy |
| 5,458,623 A | 10/1995 | Lu et al. |
| 5,466,245 A | 11/1995 | Spinelli et al. |
| 5,545,186 A | 8/1996 | Olson et al. |
| 5,609,157 A | 3/1997 | Panescu |
| 5,609,158 A | 3/1997 | Chan |
| 5,755,739 A | 5/1998 | Sun et al. |
| 5,782,888 A | 7/1998 | Sun |
| 5,817,134 A | 10/1998 | Greenhut et al. |
| 6,067,473 A | 5/2000 | Greeninger et al. |
| 6,393,316 B1 | 5/2002 | Gillberg et al. |
| 6,470,210 B1 | 10/2002 | Chen et al. |
| 6,516,225 B1 | 2/2003 | Florio |
| 6,745,068 B2 | 6/2004 | Koyrakh et al. |
| 6,865,414 B1 | 3/2005 | Levine |
| 6,895,272 B2 | 5/2005 | Seim et al. |
| 6,904,315 B2 | 6/2005 | Panken et al. |
| 6,904,319 B2 | 6/2005 | Seim et al. |
| 6,912,418 B1 | 6/2005 | Florio |
| 6,922,584 B2 | 7/2005 | Wang et al. |
| 6,931,273 B2 | 8/2005 | Groenewegen et al. |
| 7,031,765 B2 | 4/2006 | Ritscher et al. |
| 7,062,315 B2 | 6/2006 | Koyrakh et al. |
| 7,139,604 B1 | 11/2006 | Mouchawar |
| 7,184,815 B2 | 2/2007 | Kim et al. |
| 7,187,965 B2 | 3/2007 | Bischoff et al. |
| 7,242,978 B2 | 7/2007 | Cao et al. |
| 7,308,308 B1 | 12/2007 | Xi et al. |
| 7,412,282 B2 | 8/2008 | Houben |
| 7,509,160 B2 | 3/2009 | Bischoff et al. |
| 7,515,956 B2 | 4/2009 | Thompson |
| 7,532,928 B2 | 5/2009 | Lang |
| 7,537,569 B2 | 5/2009 | Sarkar et al. |
| 7,561,911 B2 | 7/2009 | Cao et al. |
| 7,570,990 B2 | 8/2009 | Faber |
| 7,580,748 B2 | 8/2009 | Garner |
| 7,593,766 B2 | 9/2009 | Faber |
| 7,596,405 B2 | 9/2009 | Kurzweil et al. |
| 7,623,911 B2 | 11/2009 | Sarkar et al. |
| 7,627,368 B2 | 12/2009 | Houben et al. |
| 7,640,054 B2 | 12/2009 | Koyrakh et al. |
| 7,657,305 B2 | 2/2010 | Nigam |
| 7,657,307 B2 | 2/2010 | Van Dam et al. |
| 7,706,869 B2 | 4/2010 | Cao et al. |
| 7,729,754 B2 | 6/2010 | Cao et al. |
| 7,826,893 B2 | 11/2010 | Cao et al. |
| 7,983,742 B2 | 7/2011 | Starc |
| 7,996,070 B2 | 8/2011 | van Dam et al. |
| 8,000,778 B2 | 8/2011 | Seim et al. |
| 8,064,998 B2 | 11/2011 | Good |
| 8,195,280 B2 | 6/2012 | Van Dam et al. |
| 8,233,980 B2 | 7/2012 | Pei |
| 8,265,753 B2 | 9/2012 | Higham |
| 8,280,510 B2 | 10/2012 | Dyjach |
| 8,285,377 B2 | 10/2012 | Rosenberg |
| 8,412,316 B2 | 4/2013 | Seim et al. |
| 8,428,697 B2 | 4/2013 | Zhang et al. |
| 8,428,705 B2 | 4/2013 | Kurzweil et al. |
| 8,521,268 B2 | 8/2013 | Zhang et al. |
| 8,548,573 B2 | 10/2013 | Keefe |
| 8,560,058 B2 | 10/2013 | Babaeizadeh et al. |
| 8,588,895 B2 | 11/2013 | Sanghera et al. |
| 8,639,316 B2 | 1/2014 | Sarkar |
| 8,688,469 B2 | 4/2014 | Ziegler et al. |
| 8,718,750 B2 | 5/2014 | Lian |
| 8,923,963 B2 | 12/2014 | Bonner et al. |
| 8,977,350 B2 | 3/2015 | Sarkar et al. |
| 2002/0120206 A1 | 8/2002 | Taha et al. |
| 2003/0023178 A1 | 1/2003 | Bischoff et al. |
| 2005/0065564 A1 | 3/2005 | Seim et al. |
| 2005/0080347 A1 | 4/2005 | Sheth et al. |
| 2006/0074332 A1 | 4/2006 | Bischoff et al. |
| 2006/0079797 A1 | 4/2006 | Bischoff et al. |
| 2006/0079798 A1 | 4/2006 | Bischoff et al. |
| 2006/0106323 A1 | 5/2006 | Bischoff et al. |
| 2006/0167364 A1 | 7/2006 | Houben |
| 2007/0142866 A1 | 6/2007 | Li et al. |
| 2007/0232944 A1 | 10/2007 | Ghanem et al. |
| 2008/0147133 A1 | 6/2008 | Garner |
| 2008/0154318 A1 | 6/2008 | Albus |
| 2008/0161703 A1 | 7/2008 | Houben et al. |
| 2009/0216144 A1 | 8/2009 | Hopenfeld |
| 2009/0270747 A1 | 10/2009 | van Dam et al. |
| 2010/0030293 A1 | 2/2010 | Sarkar et al. |
| 2010/0114195 A1 | 5/2010 | Burnes et al. |
| 2011/0125206 A1 | 5/2011 | Bornzin et al. |
| 2011/0208079 A1 | 8/2011 | Babaeizadeh et al. |
| 2011/0301661 A1 | 12/2011 | Seim et al. |
| 2011/0319949 A1 | 12/2011 | Bardy |
| 2012/0123232 A1 | 5/2012 | Najarian et al. |
| 2012/0226179 A1 | 9/2012 | Stadler et al. |
| 2012/0238891 A1 | 9/2012 | Sarkar et al. |
| 2012/0238892 A1 | 9/2012 | Sarkar |
| 2012/0290030 A1* | 11/2012 | Warman ............ A61N 1/36114 607/14 |
| 2013/0172765 A1 | 7/2013 | Stewart |
| 2014/0128758 A1 | 5/2014 | Galloway et al. |
| 2014/0155722 A1 | 6/2014 | Greenspan et al. |
| 2014/0276154 A1 | 9/2014 | Katra et al. |
| 2014/0350422 A1 | 11/2014 | Stewart |
| 2014/0378851 A1 | 12/2014 | Frei et al. |
| 2015/0073295 A1 | 3/2015 | Gordon et al. |
| 2015/0080752 A1 | 3/2015 | Lian et al. |
| 2015/0105681 A1 | 4/2015 | Bonan et al. |
| 2015/0230722 A1 | 8/2015 | Sarkar et al. |
| 2015/0305642 A1 | 10/2015 | Reinke et al. |
| 2015/0306375 A1 | 10/2015 | Marshall et al. |
| 2015/0306410 A1 | 10/2015 | Marshall et al. |

FOREIGN PATENT DOCUMENTS

| | | |
|---|---|---|
| WO | 0180042 A1 | 10/2001 |
| WO | 2004043538 | 5/2004 |
| WO | 2004108212 A2 | 12/2004 |
| WO | 2012058398 A1 | 5/2012 |

OTHER PUBLICATIONS (PCT/US2016/014493) PCT Notification of Transmittal of the International Search Report and the Written Opinion of the International Searching Authority, Mailed Apr. 15, 2016, 14 pages.

Pürerfellner et al., "P-Wave Evidence as a Method for Improving Algorithm to Detect Atrial Fibrillation in Insertable Cardiac Monitors", Heart Rhythm, vol. 11, No. 9, Sep. 2014, 9 pages.

Sarkar et al, "Method and Apparatus for Atrial Arrhythmia Episode Detection", U.S. Appl. No. 14/695,135, filed Apr. 24, 2015, 30 pages.

Sarkar et al, "Method and Apparatus for Atrial Arrhythmia Episode Detection", U.S. Appl. No. 14/695,156, filed Apr. 24, 2015, 42 pages.

(56) References Cited

OTHER PUBLICATIONS

Sarkar et al, "Method and Apparatus for Atrial Arrhythmia Episode Detection", U.S. Appl. No. 14/695,171, filed Apr. 24, 2015, 38 pages.

Sarkar et al, "Method and Apparatus for Atrial Arrhythmia Episode Detection", U.S. Appl. No. 14/695,111, filed Apr. 24, 2015, 51 pages.

Cao et al, "Atrial Arrhythmia Episode Detection in a Cardiac Medical Device", U.S. Appl. No. 14/604,363, filed Jan. 23, 2015, 46 pages.

Cao et al, "Atrial Arrhythmia Episode Detection in a Cardiac Medical Device", U.S. Appl. No. 14/604,411, filed Jan. 23, 2015, 48 pages.

Cao et al, "Atrial Arrhythmia Episode Detection in a Cardiac Medical Device", U.S. Appl. No. 14/604,468, filed Jan. 23, 2015, 46 pages.

Zhang et al, "Method and Apparatus for Beat Acquisition During Template Generation in a Medical Device Having Dual Sensing Vectors", U.S. Appl. No. 14/604,111, filed Jan. 23, 2015, 77 pages.

Zhang et al, "Method and Apparatus for Beat Acquisition During Template Generation in a Medical Device Having Dual Sensing Vectors", U.S. Appl. No. 14/604,260, filed Jan. 23, 2015, 75 pages.

Zhang et al, "Method and Apparatus for Beat Acquisition During Template Generation in a Medical Device Having Dual Sensing Vectors", U.S. Appl. No. 15/002,521, filed Jan. 21, 2016, 80 pages.

Sarkar et al, "Method and Apparatus for Adjusting a Threshold During Atrial Arrhythmia Episode Detection in an Implantable Medical Device", U.S. Appl. No. 14/926,419, filed Oct. 29, 2015, 51 pages.

Sarkar et al, "Method and Apparatus for Identifying Sick Sinus Syndrome", U.S. Appl. No. 14/626,455, filed Oct. 29, 2015, 39 pages.

Cao et al, "Atrial Arrhythmia Detection During Intermittent Instances of Ventricular Pacing in a Cardiac Medical Device", U.S. Appl. No. 14/520,798, filed Oct. 22, 2014, 35 pages.

Cao et al, "Atrial Arrhythmia Detection During Ventricular Pacing in a Cardiac Medical Device", U.S. Appl. No. 14/520,847, filed Oct. 22, 2014, 49 pages.

Cao et al, "Atrial Arrhythmia Episode Detection in a Cardiac Medical Device", U.S. Appl. No. 14/520,938, filed Oct. 22, 2014, 47 pages.

Non Final Office Action, U.S. Appl. No. 14/604,363, Mailed Apr. 8, 2016, 6 pages.

Response to OA U.S. Appl. No. 14/604,363, filed Jul. 8, 2016, 11 pages.

Non Final Office Action, U.S. Appl. No. 14/604,411, Mailed Apr. 3, 2016, 6 pages.

Response to OA U.S. Appl. No. 14/604,411, filed Jul. 8, 2016, 15 pages.

Non Final Office Action, U.S. Appl. No. 14/604,468, Mailed Apr. 13, 2016, 7 pages.

\* cited by examiner

ATRIAL ARRHYTHMIA EPISODE DETECTION IN A CARDIAC MEDICAL DEVICE

TECHNICAL FIELD

The disclosure relates generally to cardiac medical devices and, in particular, to a method for detecting atrial arrhythmia episodes during ventricular sensing and pacing in a cardiac medical device.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

As more serious consequences of persistent atrial arrhythmias have come to be understood, such as an associated risk of relatively more serious ventricular arrhythmias and stroke, there is a growing interest in monitoring and treating atrial arrhythmias. Implantable cardiac monitors and implantable cardioverter defibrillators (ICDs) may be configured to acquire cardiac electrical signals that can be analyzed for detecting atrial arrhythmias.

SUMMARY

In general, the disclosure is directed to techniques for detecting cardiac events by a medical device. A medical device operating according to the techniques disclosed herein detects a cardiac event using RR-intervals determined from a cardiac electrical signal. In response to the cardiac event detection, the medical device iteratively senses groups of a predetermined number of P-waves and analyzes the P-waves to confirm the cardiac event detection.

In one example, the disclosure provides a method of detecting a cardiac event in a medical device comprising sensing a cardiac signal, identifying R-waves in the cardiac signal attendant ventricular depolarizations, determining RR-intervals between successive R-waves in response to the sensed cardiac signal, detecting an atrial tachyarrhythmia based on an analysis of the RR-intervals, iteratively sensing groups of a predetermined number of P-waves attendant atrial depolarizations in response to detecting the atrial tachyarrhythmia, and confirming the atrial tachyarrhythmia based on an analysis of the iteratively sensed groups of P-waves.

In another example, the disclosure provides a medical device for detecting a cardiac event comprising sensing circuitry configured to receive a cardiac signal from a plurality of electrodes coupled to the medical device and a processor configured to identify R-waves in the cardiac signal attendant ventricular depolarizations, determine RR-intervals between successive R-waves in the sensed cardiac signal, detect an atrial tachyarrhythmia based on an analysis of the RR-intervals, iteratively sense groups of a predetermined number of P-waves attendant atrial depolarizations in response to detecting the atrial tachyarrhythmia, and confirm the atrial tachyarrhythmia based on an analysis of the iteratively sensed groups of P-waves.

In another example, the disclosure provides a non-transitory, computer-readable storage medium storing instructions for causing a processor included in a medical device to perform a method for detecting a cardiac event. The method includes sensing a cardiac signal, identifying R-waves in the cardiac signal attendant ventricular depolarizations, determining RR-intervals between successive R-waves in response to the sensed cardiac signal, detecting an atrial tachyarrhythmia based on an analysis of the RR-intervals, iteratively sensing groups of a predetermined number of P-waves attendant atrial depolarizations in response to detecting the atrial tachyarrhythmia, and confirming the atrial tachyarrhythmia based on an analysis of the iteratively sensed groups of P-waves.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
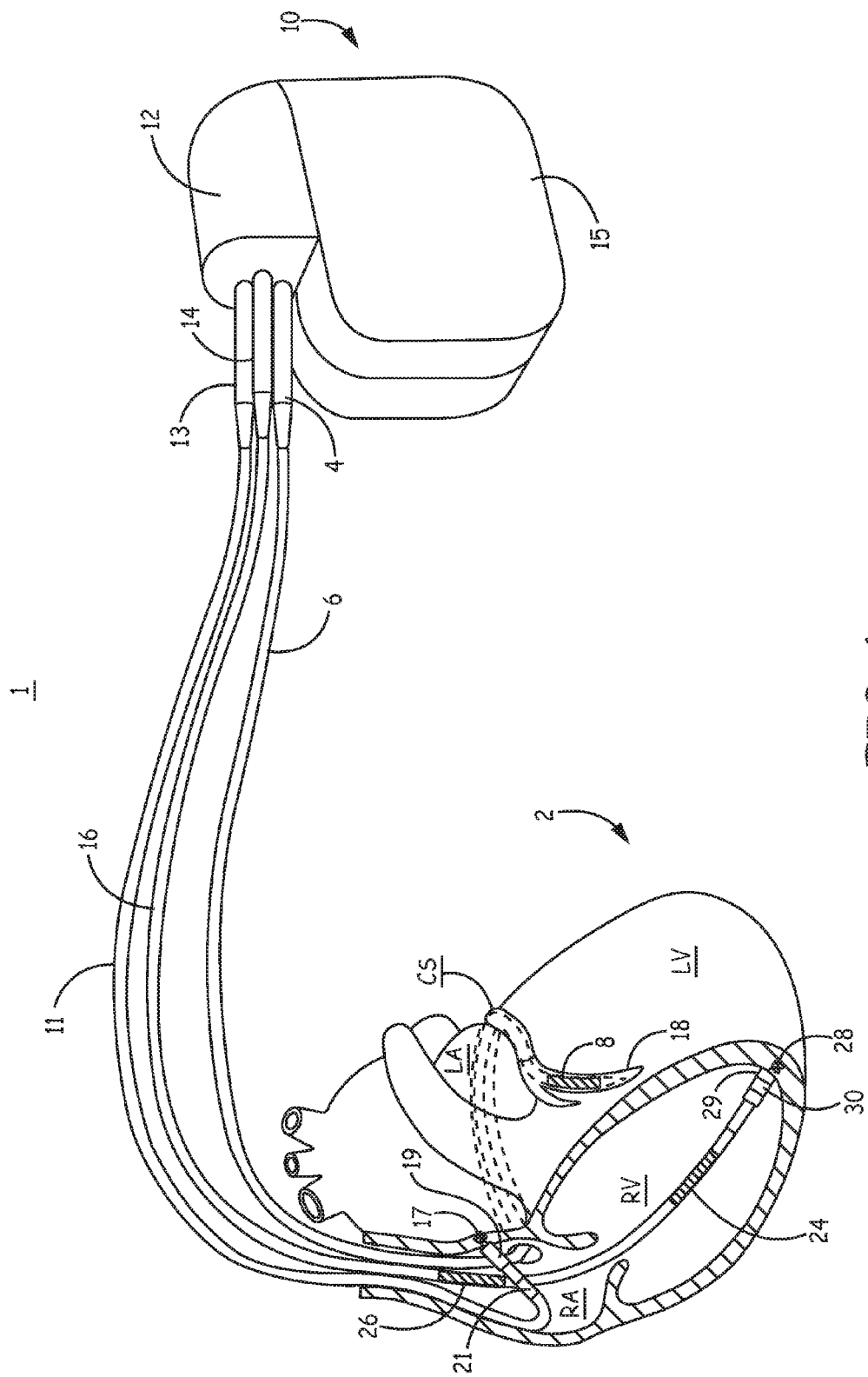
FIG. 1 is a conceptual diagram of an implantable medical device (IMD) system for detecting cardiac arrhythmias according to one example.

In the following description, references are made to illustrative embodiments for carrying out the methods described herein. It is understood that other embodiments may be utilized without departing from the scope of the disclosure.

In various examples, ventricular signals are used for determining successive ventricular cycle lengths for use in detecting atrial arrhythmias. In response to detecting an atrial arrhythmia, groups of a predetermined number of P-waves are identified and analyzed for confirming the atrial arrhythmia. The methods presented herein may be embodied in software, hardware or firmware in implantable or external medical devices. Such devices include implantable monitoring devices having cardiac electrical signal monitoring capabilities and associated cardiac electrical signal sense electrodes, which may be, for example, intracardiac; epicardial; substernal, non-transvenous; sub-muscular; or subcutaneous electrodes.

Single chamber devices have been designed to detect AF using a ventricular EGM signal. Illustrative methods and devices for detecting AF using a ventricular EGM signal are generally described in commonly assigned U.S. patent application Ser. No. 14/520,798 to Cao et. al., U.S. patent application Ser. No. 14/520,847 to Cao et al., and U.S. patent application Ser. No. 14/520,938 to Cao et al., all of which are incorporated herein by reference in their entirety. R-waves attendant to the ventricular depolarization are sensed from the ventricular EGM signal and used to determine RR-intervals (RRIs), i.e., intervals between successive R-waves. Successive RRI differences are determined by subtracting an RRI from an immediately preceding RRI. An analysis of a Lorenz plot of the successive RRI differences may reveal RRI variability that is typical of AF. In some cases, however, AF detection criteria based on RRI variability may be satisfied when AF is not actually present leading to a false AF detection when a ventricular therapy may be needed. The techniques disclosed herein provide methods for reducing false detections of AF that are made based on RRI variability analysis. An ICD or other medical device operating according to the techniques disclosed herein enables a P-wave template matching analysis in response to an AF detection made based on RRI variability analysis.

The methods described herein can be incorporated in a variety of implantable or external medical devices having cardiac signal monitoring capabilities, which may include therapy delivery capabilities, such as single chamber, dual chamber or bi-ventricular pacing systems or ICDs that sense the R-waves in the ventricles and deliver an electrical stimulation therapy to the ventricles. The atrial arrhythmia detection methods presently disclosed may also be incorporated in implantable cardiac monitors having implantable electrodes or external cardiac monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices.

FIG. 1 is a conceptual diagram of an implantable medical device (IMD) system 1 for detecting arrhythmia according to one example. The IMD system 1 of FIG. 1 includes an implantable cardioverter defibrillator (ICD) 10 coupled to a patient's heart 2 via transvenous electrical leads 6, 11, and 16. ICD 10 includes a connector block 12 that may be configured to receive the proximal ends of a right ventricular (RV) lead 16, a right atrial (RA) lead 11 and a coronary sinus (CS) lead 6, which are advanced transvenously for positioning electrodes for sensing and stimulation in three or all four heart chambers.

RV lead 16 is positioned such that its distal end is in the right ventricle for sensing RV cardiac signals and delivering pacing or shocking pulses in the right ventricle. For these purposes, RV lead 16 is equipped with pacing and sensing electrodes shown as a ring electrode 30 and a tip electrode 28. In some examples, tip electrode 28 is an extendable helix electrode mounted retractably within an electrode head 29. RV lead 16 is further shown to carry defibrillation electrodes 24 and 26, which may be elongated coil electrodes used to deliver high voltage cardioversion/defibrillation (CV/DF) electrodes. Defibrillation electrode 24 is referred to herein as the "RV defibrillation electrode" or "RV coil electrode" because it may be carried along RV lead 16 such that it is positioned substantially within the right ventricle when distal pacing and sensing electrodes 28 and 30 are positioned for pacing and sensing in the right ventricle. Defibrillation electrode 26 is referred to herein as a "superior vena cava (SVC) defibrillation electrode" or "SVC coil electrode" because it may be carried along RV lead 16 such that it is positioned at least partially along the SVC when the distal end of RV lead 16 is advanced within the right ventricle.

Each of electrodes 24, 26, 28 and 30 are connected to a respective insulated conductors extending within the body of lead 16. The proximal end of the insulated conductors are coupled to corresponding connectors carried by proximal lead connector 14, e.g., an IS-4 connector, at the proximal end of lead 16 for providing electrical connection to ICD 10. It is understood that although ICD 10 is illustrated in FIG. 1 is a multi-chamber chamber device coupled to RA lead 11 and CS lead 6, ICD 10 may be configured as a single chamber device coupled only to RV lead 16 and may be configured to perform the techniques disclosed herein using electrodes 24, 26, 28 and/or 30 (and in some examples housing 15) for receiving cardiac electrical signals for detecting AF.

RA lead 11 is positioned such that its distal end is in the vicinity of the right atrium and the superior vena cava. Lead 11 is equipped with pacing and sensing electrodes 17 and 21 shown as a tip electrode 17, which may be an extendable helix electrode mounted retractably within electrode head 19, and a ring electrode 21 spaced proximally from tip electrode 17. The electrodes 17 and 21 provide sensing and pacing in the right atrium and are each connected to a respective insulated conductor with the body of RA lead 11.

Each insulated conductor is coupled at its proximal end to connector carried by proximal lead connector 13.

CS lead 6 is advanced within the vasculature of the left side of the heart via the coronary sinus and a cardiac vein 18. CS lead 6 is shown in the embodiment of FIG. 1 as having one or more electrodes 8 that may be used in combination with either RV coil electrode 20 or the SVC coil electrode 23 for delivering electrical shocks for cardioversion and defibrillation therapies. In other examples, coronary sinus lead 6 may also be equipped with one or more electrodes 8 for use in delivering pacing and or sensing cardiac electrical signals in the left chambers of the heart, i.e., the left ventricle and/or the left atrium. The one or more electrodes 8 are coupled to respective insulated conductors within the body of CS lead 6, which provides connection to the proximal lead connector 4.

The RA pacing and sensing electrodes 17 and 21 and the RV pacing and sensing electrodes 28 and 30 may be used as bipolar pairs, commonly referred to as a "tip-to-ring" configuration for sensing cardiac electrical signals. Further, RV tip electrode 28 may be selected with a coil electrode 8, 24, or 26 to be used as an integrated bipolar pair, commonly referred to as a "tip-to-coil" configuration for sensing cardiac electrical signals. ICD 10 may, for example, select one or more sensing electrode vectors including a tip-to-ring sensing vector between electrodes 26 and 24 and a tip-to-coil sensing vector, e.g., between RV tip electrode 26 and SVC coil electrode 26, between RV tip electrode 28 and RV coil electrode 24, between RV ring electrode 30 and SVC coil electrode 26 or between RV ring electrode 30 and RV coil electrode 24 In some cases, any of electrodes 8, 17, 21, 24, 26, 28 or 30 may be selected by ICD 10 in a unipolar sensing configuration with the ICD housing 15 serving as the indifferent electrode, commonly referred to as the "can" or "case" electrode. It is recognized that numerous sensing and electrical stimulation electrode vectors may be available using the various electrodes carried by one or more of leads 6, 15 and 16 coupled to ICD 10, and ICD 10 may be configured to selectively couple one or more sensing electrode vector to sensing circuitry enclosed by housing 15, e.g., sensing circuitry including one or more amplifiers, filters, rectifiers, comparators, sense amplifiers, analog-to-digital convertors and/or other circuitry configured to acquire a cardiac electrical signal for use in detecting cardiac arrhythmias.

In other examples, the ICD housing 15 may serve as a subcutaneous defibrillation electrode in combination with one or more of the coil electrodes 8, 24 or 26 for delivering CV/DF shocks to the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, subcutaneous implantable device, or other internal or external cardiac monitoring device.

Figure 2:
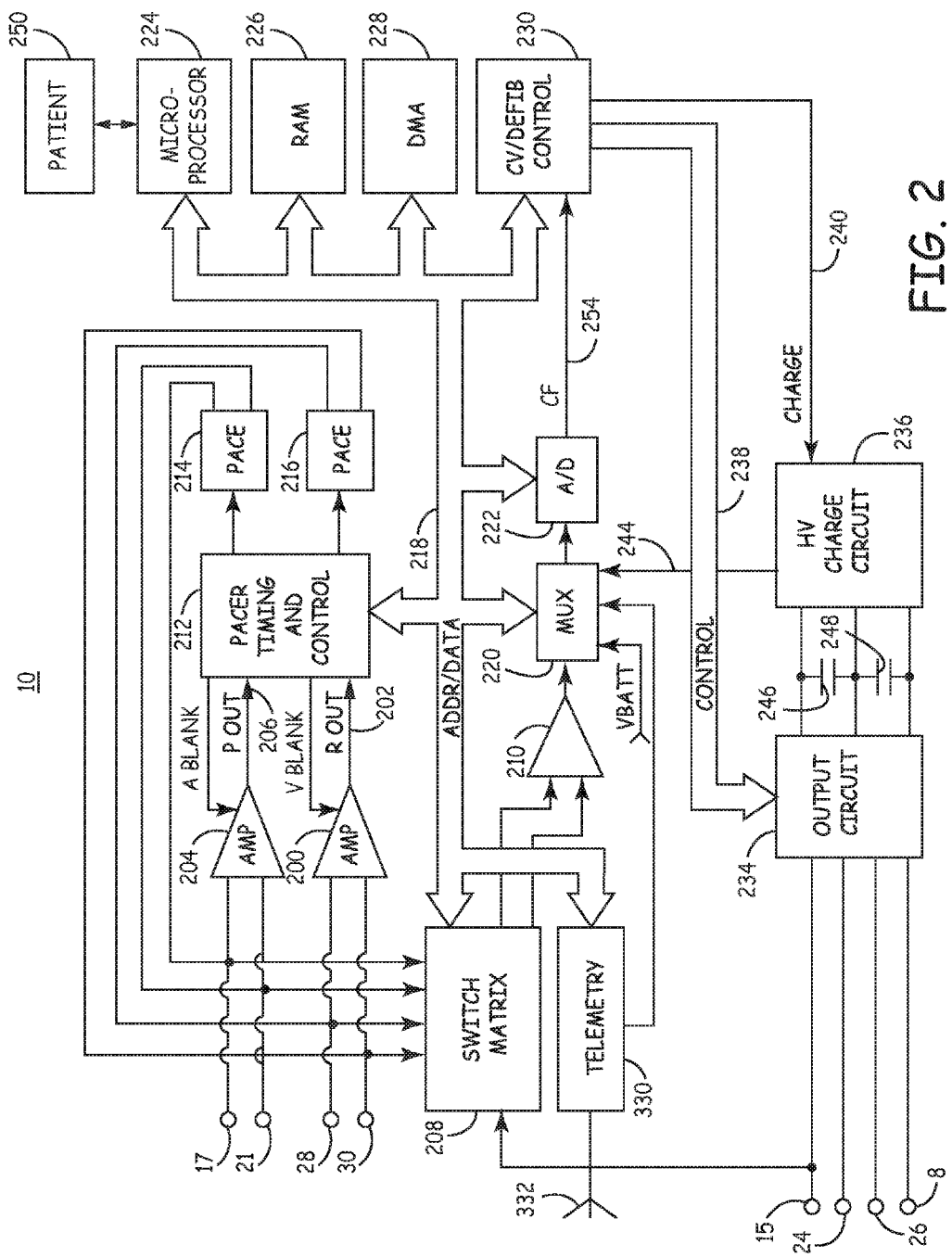
FIG. 2 is a schematic diagram of circuitry that may be included in the implantable cardioverter defibrillators shown in FIG. 1 and FIGS. 3A and 3B.

FIG. 2 is a functional schematic diagram of the ICD 10 of FIG. 1. This diagram should be taken as illustrative of the type of device with which the invention may be embodied and not as limiting. The example shown in FIG. 2 is a microprocessor-controlled device, but the methods of the present invention may also be practiced with other types of devices such as those employing dedicated digital circuitry.

With regard to the electrode system illustrated in FIG. 1, ICD 10 is provided with a number of connection terminals for achieving electrical connection to the leads 6, 15, and 16 and their respective electrodes. Housing 15 may be used as an indifferent electrode during unipolar stimulation or sensing. Electrodes 24, 26 and 8 may be selectively coupled to the high voltage output circuit 234 to facilitate the delivery of high energy shocking pulses to the heart using one or more of the coil electrodes 8, 24 and 26 and optionally the housing 15.

RA tip electrode 17 and RA ring electrode 21 may be coupled to atrial sense amplifier 204 for sensing atrial signals such as P-waves. RV tip electrode 28 and the RV ring electrode 30 may be coupled to a ventricular sense amplifier 200 for sensing ventricular signals. The atrial sense amplifier 204 and the ventricular sense amplifier 200 may take the form of automatic gain controlled amplifiers with adjustable sensitivity. ICD 10 and, more specifically, microprocessor 224 may automatically adjust the sensitivity of atrial sense amplifier 204, ventricular sense amplifier 200 or both in response to detection of oversensing in order to reduce the likelihood of oversensing of cardiac events and/or non-cardiac noise.

Atrial sense amplifier 204 and ventricular sense amplifier 200 may receive timing information from pacer timing and control circuitry 212. For example, atrial sense amplifier 204 and ventricular sense amplifier 200 may receive blanking period input, e.g., ABLANK and VBLANK, respectively, which indicates the amount of time the amplifiers are "turned off" in order to prevent saturation due to an applied pacing pulse or defibrillation shock. The general operation of the ventricular sense amplifier 200 and the atrial sense amplifier 204 may correspond to that disclosed in U.S. Pat. No. 5,117,824 (Keimel, et al.), incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202. As described below, a signal on the R-out signal line 202, which may be referred to as a ventricular sense event (Vs event) signal, may be received by microprocessor 224 an used for determining RRI differences as well as for setting P-wave windows for identifying P-waves in iterative groups of a predetermined number of P-waves for use in confirming an atrial arrhythmia detection.

Switch matrix 208 is used to select which of the available electrodes 8, 17, 21, 24, 26, 28 and 30 are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. For example, while RV electrodes 28 and 30 are shown coupled to sense amplifier 200 and pace output circuit 216 suggesting dedicated pace/sense electrodes and coil electrodes 24 and 26 are shown coupled to HV output circuit 234 suggesting dedicated CV/DV shock electrodes, it is recognized that switching circuitry included in switch matrix 208 may be used to select any of the available electrodes in a sensing electrode vector, a pacing electrode vector, or a CV/DF shock vector as indicated previously.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of numerous signal processing methodologies for analyzing cardiac signals and cardiac event waveforms, e.g., P-waves and R-waves. One tachyarrhythmia detection system is described in U.S. Pat. No. 5,545,186 (Olson et al.), incorporated herein by reference in its entirety. As described herein, analysis of digital signals of groups of P-waves may be performed in response to an RRI-based detection of an atrial arrhythmia for confirming the atrial arrhythmia.

Upon detection of an arrhythmia, an episode of EGM data, along with sensed intervals and corresponding annotations of sensed events, may be stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 28 and 30. A far-field sensing electrode pair includes electrodes spaced further apart such as any of: the defibrillation coil electrodes 8, 24 or 26 with housing 15; a tip electrode 17 or 28 with housing 15; a tip electrode 17 or 28 with a defibrillation coil electrode 8, 24 or 26; or atrial tip electrode 17 with ventricular ring electrode 30. The use of near-field and far-field EGM sensing of arrhythmia episodes is described in U.S. Pat. No. 5,193,535 (Bardy), incorporated herein by reference in its entirety. Annotation of sensed events, which may be displayed and stored with EGM data, is described in U.S. Pat. No. 4,374,382 (Markowitz), incorporated herein by reference in its entirety.

The telemetry circuit 330 includes a transceiver for receiving downlink telemetry from and sending uplink telemetry to an external device by means of an antenna 332. Telemetry circuit 330 provides bi-directional telemetric communication with an external device such as a medical device programmer for transmitting and receiving data via a communication link that may be established between ICD 10 and the external device using a radio frequency (RF) link such as BLUETOOTH®, Wi-Fi, or Medical Implant Communication Service (MICS) or other RF or communication frequency bandwidth.

ICD 10 may receive program operating parameters and algorithms via telemetry circuit 330 for storage in RAM 226 and accessed by microprocessor 224 for controlling ICD functions. For example, cardiac rhythm detection parameters and therapy control parameters used by ICD 10 may be programmed via telemetry circuit 330.

Data stored or acquired by ICD 10, including physiological signals or associated data derived therefrom, results of device diagnostics, and histories of detected arrhythmia episodes and delivered therapies, may be retrieved from ICD 10 by the external device following an interrogation command received by telemetry circuit 330. In various examples, the external device (not shown) may be a clinic- or hospital-based programmer, a home monitor or a hand held device. Data to be uplinked to the external device and control signals for the telemetry circuit 330 are provided by microprocessor 224 via address/data bus 218. Received telemetry is provided to microprocessor 224 via multiplexer 220. Numerous types of telemetry systems known for use in implantable medical devices may be implemented in ICD 10.

Other circuitry shown in FIG. 2 is illustrative of therapy delivery circuitry that may be included in an ICD or other implantable medical device employing the atrial arrhythmia detection technique disclosed herein when the device is configured for providing cardiac pacing, cardioversion and defibrillation therapies. For example, the pacer timing and control circuitry 212 may include programmable digital counters which control the basic time intervals associated with various single, dual or multi-chamber pacing modes or anti-tachycardia pacing therapies delivered in the atria or ventricles. Pacer timing and control circuitry 212 also sets the amplitude, pulse width, polarity or other characteristics of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pace output circuit 214 and ventricular pace output circuit 216. The pace output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia. In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In some examples, the ICD 10 may be equipped with a patient notification system 250. Any patient notification method known for use in implantable medical devices may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 (Greeninger et al.), incorporated herein by reference in its entirety.

Figure 3A:
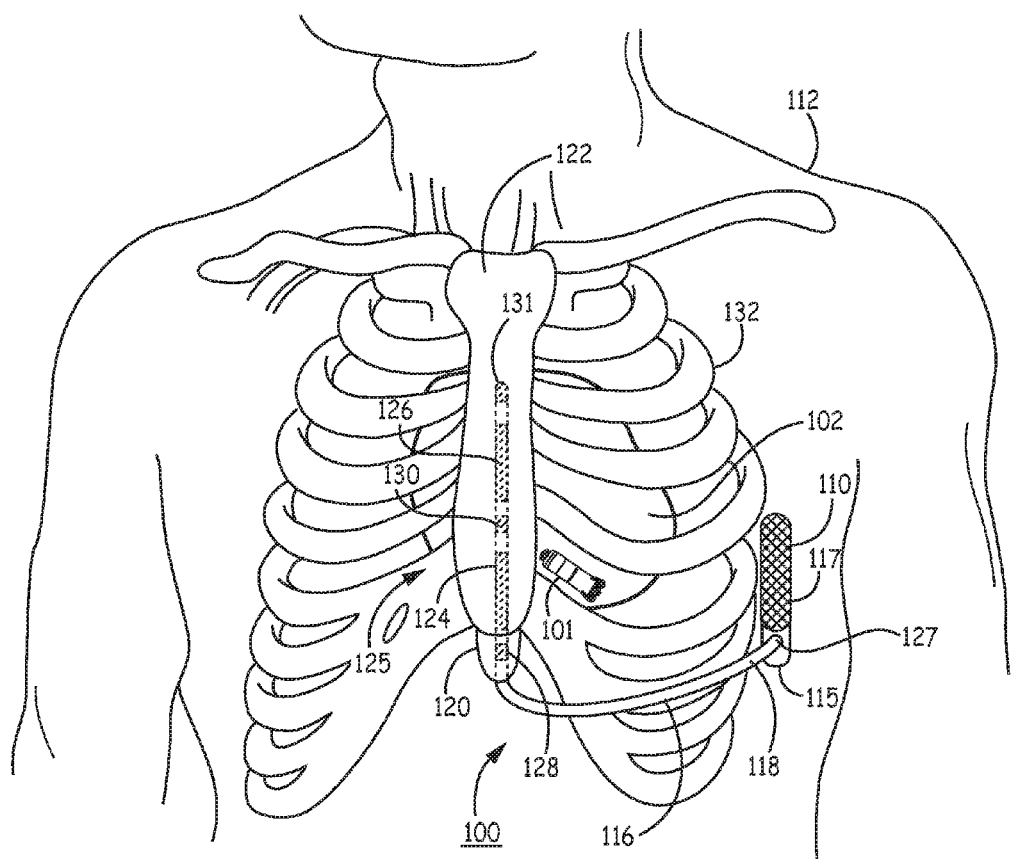
FIGS. 3A and 3B are conceptual diagrams of an alternative IMD system that may be configured to detect atrial fibrillation (AF) according to the techniques disclosed herein.
Figure 3B:
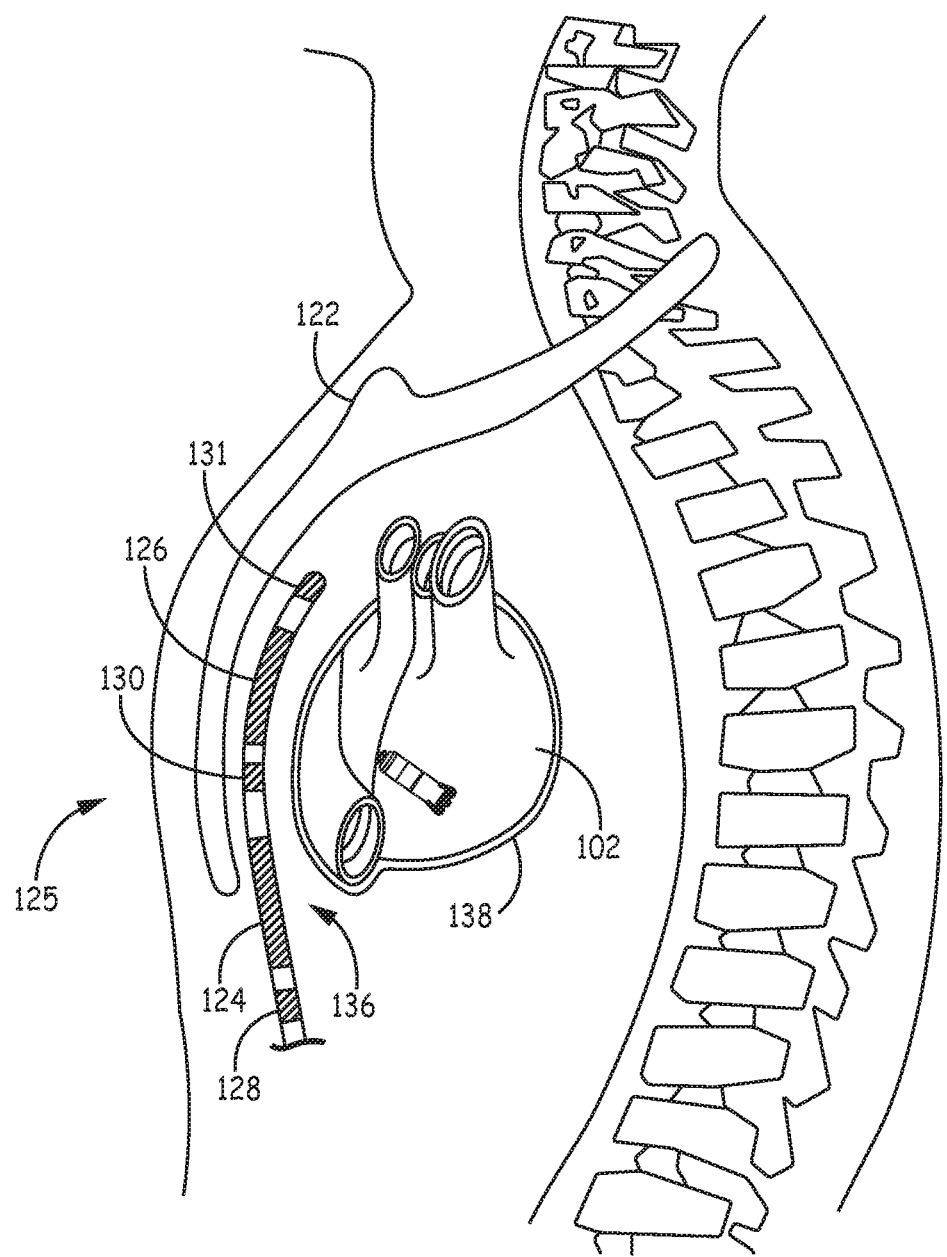

FIGS. 3A and 3B are conceptual diagrams of an alternative ICD system 100 that may be configured to detect and confirm AF according to the techniques disclosed herein. FIG. 3A is a front view of an extra-cardiovascular ICD system 100 implanted within patient 112. FIG. 3B is a side view of ICD system 100 implanted within patient 112. ICD system 100 includes an ICD 110 connected to an extra-cardiovascular electrical stimulation and sensing lead 116. ICD system 100 may further include an intracardiac pacemaker 101 configured to deliver pacing pulses to a ventricular or atrial chamber.

ICD 110 includes a housing 115 that forms a hermetic seal that protects internal components of ICD 110. Internal device components may include circuitry shown in FIG. 2, such as sense amplifier(s), A/D converter, pacing output circuitry, high voltage output circuitry and a microprocessor and memory and/or other control circuitry. The housing 115 of ICD 110 may be formed of a conductive material, such as titanium or titanium alloy. The housing 115 may function as a housing electrode (sometimes referred to as a can electrode). In examples described herein, housing 115 may be used as an active can electrode for use in delivering cardioversion/defibrillation (CV/DF) shocks or other high voltage pulses delivered by HV charge circuit 236 (FIG. 2). In other examples, housing 115 may be available for use in sensing cardiac signals or for delivering unipolar, low voltage cardiac pacing pulses by a pacer output circuit in conjunction with lead-based cathode electrodes. In other instances, the housing 115 of ICD 110 may include a plurality of electrodes on an outer portion of the housing. The outer portion(s) of the housing 115 functioning as an electrode(s) may be coated with a material, such as titanium nitride.

ICD 110 includes a connector assembly 117 (also referred to as a connector block or header) that includes electrical feedthroughs crossing housing 115 to provide electrical connections between conductors extending within the lead body 118 of lead 116 and electronic components included within the housing 115 of ICD 110. As described above in conjunction with FIG. 2, housing 115 may house one or more processors, memories, telemetry transceivers, sensing circuitry such as sense amplifiers and analog-to digital converters, therapy delivery circuitry such as pacer timing and control, CV/DF control, pace output and HV output circuits and associated charging circuits, a switch matrix, a data bus, one or more batteries or other power sources and other components for sensing cardiac electrical signals, detecting a heart rhythm, and controlling and delivering electrical stimulation pulses to treat an abnormal heart rhythm.

Lead 116 includes an elongated lead body 118 having a proximal end 127 that includes a lead connector (not shown) configured to be connected to ICD connector assembly 117 and a distal portion 125 that includes one or more electrodes. In the example illustrated in FIGS. 3A and 3B, the distal portion 125 of lead 116 includes defibrillation electrodes 124 and 126 and pace/sense electrodes 128, 130 and 131. In some cases, defibrillation electrodes 124 and 126 may together form a defibrillation electrode in that they may be configured to be activated concurrently. Alternatively, defibrillation electrodes 124 and 126 may form separate defibrillation electrodes in which case each of the electrodes 124 and 126 may be activated independently. In some instances, defibrillation electrodes 124 and 126 are coupled to electrically isolated conductors, and ICD 110 may include switching mechanisms to allow electrodes 124 and 126 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 115 as an active electrode).

Electrodes 124 and 126 (and in some examples housing 115) are referred to herein as defibrillation electrodes because they are utilized, individually or collectively, for delivering high voltage stimulation therapy (e.g., cardioversion or defibrillation shocks). Electrodes 124 and 126 may be elongated coil electrodes and generally have a relatively high surface area for delivering high voltage electrical stimulation pulses compared to low voltage pacing and sensing electrodes 28, 30 and 31. However, electrodes 124 and 126 and housing 115 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 124 and 126 for use in only high voltage cardioversion/defibrillation shock therapy applications. Electrodes 124 and 126 may be used in a pacing electrode vector for delivering extra-cardiovascular pacing pulses such as ATP pulses, post-shock pacing or other pacing therapies and/or in a sensing vector used to sense cardiac electrical signals for detecting atrial and ventricular arrhythmias, referred to generally as "cardiac events", including atrial fibrillation (AF), ventricular tachycardia (VT) and ventricular fibrillation (VF).

Electrodes 128, 130 and 131 are relatively smaller surface area electrodes for delivering low voltage pacing pulses and for sensing cardiac electrical signals. Electrodes 128, 130 and 131 are referred to as pace/sense electrodes because they are generally configured for use in low voltage applications, e.g., used as either a cathode or anode for delivery of pacing pulses and/or sensing of cardiac electrical signals. Electrodes 124, 126, 128, 130 and/or 131 may be used to acquire cardiac electrical signals used for AF detection according to the techniques disclosed herein.

In the example illustrated in FIGS. 3A and 3B, electrode 128 is located proximal to defibrillation electrode 124, and electrode 130 is located between defibrillation electrodes 124 and 126. A third pace/sense electrode 131 may be located distal to defibrillation electrode 126. In other examples, none, one or more pace/sense electrodes may be located proximal to defibrillation electrode 124, none, one or more pace/sense electrodes may be located between defibrillation electrodes 124 and 126, and/or none, one or more pace/sense electrodes may be located distal to defibrillation electrode 126. Electrodes 128 and 130 are illustrated as ring electrodes, and electrode 31 is illustrated as a hemispherical tip electrode in the example of FIGS. 3A and 3B but may be provided as other types of electrodes.

Lead 16 extends subcutaneously or submuscularly over the ribcage 132 medially from the connector assembly 127 of ICD 110 toward a center of the torso of patient 112, e.g., toward xiphoid process 120 of patient 112. At a location near xiphoid process 120, lead 116 bends or turns and extends superiorly within anterior mediastinum 136 in a substernal position. Lead 116 of system 100 is implanted at least partially underneath sternum 122 of patient 112.

Anterior mediastinum 136 may be viewed as being bounded laterally by pleurae, posteriorly by pericardium 138, and anteriorly by sternum 122. In some instances, the anterior wall of anterior mediastinum 136 may also be formed by the transversus thoracis muscle and one or more costal cartilages. Anterior mediastinum 136 includes a quantity of loose connective tissue (such as areolar tissue), adipose tissue, some lymph vessels, lymph glands, substernal musculature, small side branches of the internal thoracic artery or vein, and the thymus gland. In one example, the distal portion 125 of lead 116 extends along the posterior side of sternum 122 substantially within the loose connective tissue and/or substernal musculature of anterior mediastinum 136.

A lead implanted such that the distal portion 125 is substantially within anterior mediastinum 136 may be referred to as a "substernal lead." In the example illustrated in FIGS. 3A and 3B, lead 116 is located substantially centered under sternum 122. In other instances, however, lead 116 may be implanted such that it is offset laterally from the center of sternum 122. In some instances, lead 116 may extend laterally such that distal portion 125 of lead 116 is underneath/below the ribcage 132 in addition to or instead of sternum 122. In other examples, the distal portion 125 of lead 116 may be implanted in other extra-cardiovascular, intra-thoracic locations, including the pleural cavity or around the perimeter of and adjacent to but typically not within the pericardium 138 of heart 102.

In other examples, lead 116 may remain outside the thoracic cavity and extend subcutaneously or submuscularly over the ribcage 132 and/or sternum 122. The path of lead 116 may depend on the location of ICD 110, the arrangement and position of electrodes carried by the lead distal portion 125, and/or other factors.

Electrical conductors (not illustrated) extend through one or more lumens of the elongated lead body 118 of lead 116 from the lead connector at the proximal lead end 127 to electrodes 124, 126, 128, 130 and 131 located along the distal portion 125 of the lead body 118. The lead body 118 of lead 116 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 118 are each electrically coupled with respective defibrillation electrodes 124 and 126 and pace/sense electrodes 128, 130 and 131. Each of pacing and sensing electrodes 128, 130 and 131 are coupled to respective electrical conductors, which may be separate respective conductors within the lead body. The respective conductors electrically couple the electrodes 124, 126, 128, 130 and 131 to circuitry, such as a switch matrix or other switching circuitry for selection and coupling to a sense amplifier or other cardiac event detection circuitry and/or to a therapy output circuit, e.g., a pacing output circuit or a HV output circuit for delivering CV/DF shock pulses. Connections between electrode conductors and ICD circuitry is made via connections in the connector assembly 117, including associated electrical feedthroughs crossing housing 115. The electrical conductors transmit therapy from an output circuit within ICD 110 to one or more of defibrillation electrodes 124 and 126 and/or pace/sense electrodes 128, 130 and 131 and transmit sensed electrical signals from one or more of defibrillation electrodes 124 and 126 and/or pace/sense electrodes 128, 130 and 131 to the sensing circuitry within ICD 110.

ICD 110 may obtain electrical signals corresponding to electrical activity of heart 102 via a combination of sensing vectors that include combinations of electrodes 128, 130, and/or 131. In some examples, housing 115 of ICD 110 is used in combination with one or more of electrodes 128, 130 and/or 131 in a sensing electrode vector. ICD 110 may even obtain cardiac electrical signals using a sensing vector that includes one or both defibrillation electrodes 124 and/or 126, e.g., between electrodes 124 and 126 or one of electrodes 124 or 126 in combination with one or more of electrodes 128, 130, 131, and/or the housing 115.

ICD 110 analyzes the cardiac electrical signals received from one or more of the sensing vectors to monitor for abnormal rhythms, such as AF, VT and VF. ICD 110 generates and delivers electrical stimulation therapy in response to detecting a tachyarrhythmia (e.g., VT or VF). ICD 110 may deliver ATP in response to VT detection, and in some cases may deliver ATP prior to a CV/DF shock or during high voltage capacitor charging in an attempt to avert the need for delivering a CV/DF shock. ICD 110 may deliver a CV/DF shock pulse when VF is detected or when VT is not terminated by ATP.

In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the AF detection techniques disclosed herein are described in commonly-assigned U.S. patent application Ser. No. 14/519,436, U.S. patent application Ser. No. 14/695,255 and provisionally-filed U.S. Pat. Application No. 62/089,417, all of which are incorporated herein by reference in their entirety.

ICD 110 is shown implanted subcutaneously on the left side of patient 112 along the ribcage 132. ICD 110 may, in some instances, be implanted between the left posterior axillary line and the left anterior axillary line of patient 112. ICD 110 may, however, be implanted at other subcutaneous or submuscular locations in patient 112. For example, ICD 110 may be implanted in a subcutaneous pocket in the pectoral region. In this case, lead 116 may extend subcutaneously or submuscularly from ICD 110 toward the manubrium of sternum 122 and bend or turn and extend inferior from the manubrium to the desired location subcutaneously or submuscularly. In yet another example, ICD 110 may be placed abdominally.

In some patients, an intracardiac pacemaker 101 may be present in the right ventricle, right atrium or left ventricle. Pacemaker 101 may be configured to deliver pacing pulses in the absence of sensed intrinsic heart beats, in response to detecting VT, or according to other pacing therapy algorithms. For example, pacemaker 101 may be implanted in the right ventricle of the patient for providing single chamber ventricular pacing. The techniques disclosed herein for classifying a rhythm as AF or non-AF may be utilized in the presence of ventricular pacing delivered by ICD 110 and/or by an intracardiac pacemaker such as pacemaker 101. Pacemaker 101 may generally correspond to the intra-cardiac pacemaker disclosed in U.S. Pat. No. 8,923,963 (Bonner, et al.), incorporated herein by reference in its entirety. Pacemaker 101 may have limited processing power and therapy delivery capacity compared to ICD 110 such that the advanced cardiac rhythm detection techniques disclosed herein may be implemented in ICD 110 rather than in pacemaker 101. As such, the methods disclosed herein are described in conjunction with ICD 10 or ICD 110. These techniques, however, are not to be considered limited to being implemented in an ICD. Aspects of the AF detection techniques disclosed herein may be implemented in pacemaker 101, all or in part, when a P-wave signal having sufficient signal-to-noise quality can be acquired by the intracardiac pacemaker 101.

Figure 4:
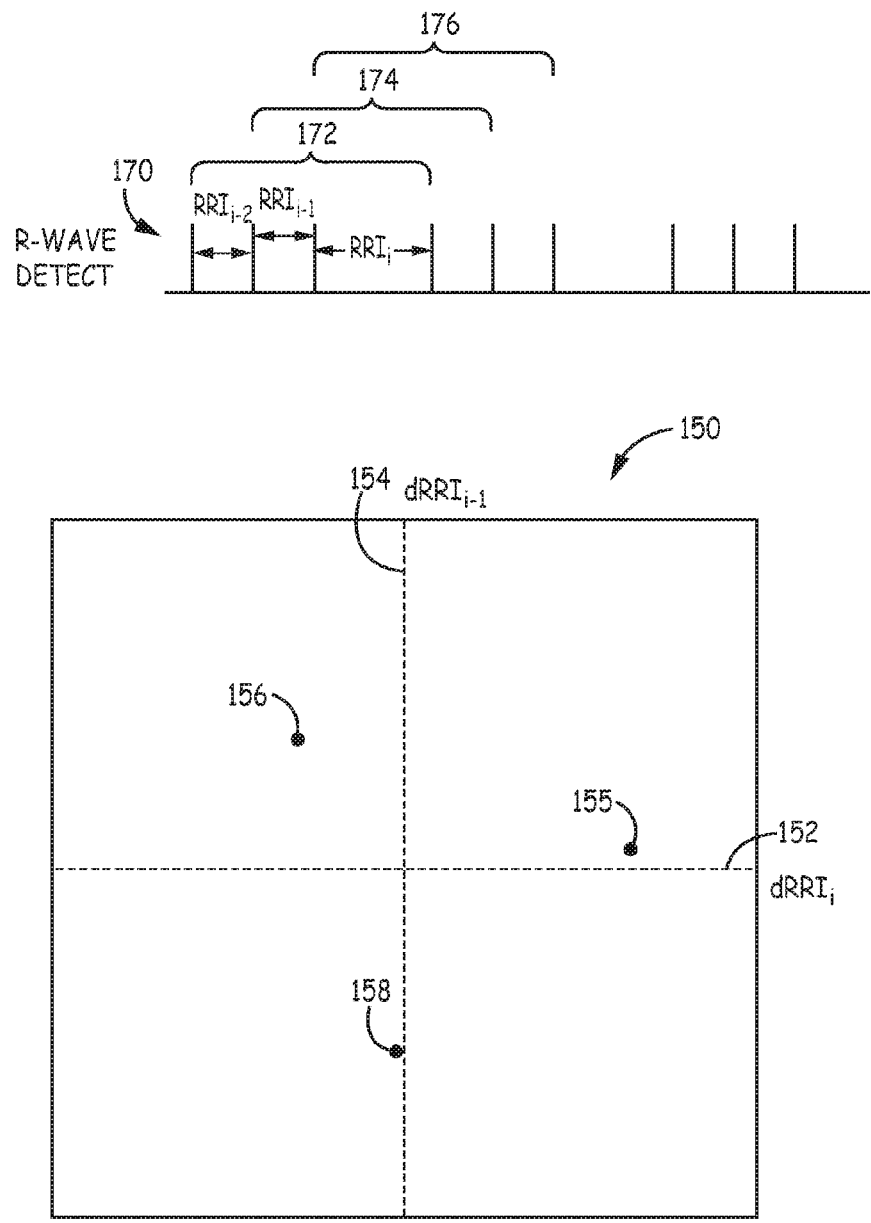
FIG. 4 is a schematic diagram of methods used for classifying cardiac events by the ICD of FIG. 1 or the ICD of FIGS. 3A and 3B according to one example.

FIG. 4 is a schematic diagram of methods used for classifying cardiac events by ICD 10 (or ICD 110) according to one example. Methods have been developed for detecting atrial arrhythmias based on the irregularity of ventricular cycles determined from RRI differences that exhibit discriminatory signatures when plotted in a Lorenz scatter plot such as the plot shown in FIG. 4. One such method is generally disclosed by Ritscher et al. in U.S. Pat. No. 7,031,765, incorporated herein by reference in its entirety. Other methods are generally disclosed by Sarkar, et al. in U.S. Pat. No. 7,623,911 and in U.S. Pat. No. 7,537,569 and by Houben in U.S. Pat. No. 7,627,368, all of which patents are also incorporated herein by reference in their entirety.

In order to determine whether AF is occurring, the microprocessor 224 may determine differences between RRIs based on sensed R-waves (R OUT signal line 202 in FIG. 2). Microprocessor 224 may make the decision as to whether an AF event is occurring based at least in part on the resulting pattern or signature of RRI differences. As described below, when the resulting signature of RRI differences indicates AF is occurring, an iterative analysis of groups of a predetermined number of P-waves is performed to confirm the RRI-based AF detection. Techniques disclosed herein may be utilized as part of an overall tachyarrhythmia detection and discrimination algorithm implemented in ICD 10 (or ICD 110).

The concept of using a signature of RRI differences for detecting AF is illustrated by the generation of a Lorenz scatter plot as shown in FIG. 4. Microprocessor 224 determines the differences between consecutive pairs of RR-intervals ($\delta RRs$) which can be plotted for a time series of RRIs. The Lorenz plot 150 is a Cartesian coordinate system defined by $\delta RR_i$ along the x-axis 152 and $\delta RR_{i-1}$ along the y-axis 154. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RRI and the previous RRI, $\delta RR_{i-1}$. $\delta RR_{i-1}$ is the difference $RRI_{i-1}$ between and the previous RRI, $RRI_{i-2}$.

As such, each data point plotted on the Lorenz plot 150 represents an RRI pattern relating to three consecutive RRIs: $RRI_i$, $RRI_{i-1}$ and $RRI_{i-2}$, measured between four consecutively sensed R-waves. RRI information is not limited to detection of R-waves and determination of RRIs. The terms RRI and $\delta RR_i$ as used herein refer generally to a measurement of ventricular cycle length (VCL) and the difference between two consecutive VCL measurements, respectively, whether the VCL measurements were derived from a series of sensed R-waves from a cardiac electrical signal or a series of ventricular cycle event detections made from another physiological signal (e.g., a peak pressure determined from a pressure signal). For the sake of illustration, the methods described herein refer to R-wave detections for performing VCL measurements and the determination of ($\delta RR_i$, $\delta RR_{i-1}$) points.

As illustrated in FIG. 4, a series of R-waves 170 (represented by vertical bars) are sensed and in order to plot a point on the Lorenz plot area 150, a ($\delta RR_i$, $\delta RR_{i-1}$) point is determined by determining successive RRIs determined from the sensed R-waves 170. In the example shown, a first series 172 of three consecutive RRIs ($RRI_{i-2}$, $RRI_{i-1}$ and $RRI_i$) provides the first data point 155 on the Lorenz plot area 150. $\delta RR_{i-1}$, which is the difference between $RRI_{i-2}$ and $RRI_{i-1}$ is near 0. $\delta RR_i$, the difference between the $RRI_{i-1}$ and $RRI_i$, is a positive change. Accordingly, a ($\delta RR_i$, $\delta RR_{i-1}$) point 155 having a y-coordinate near 0 and a positive x-coordinate is plotted in the Lorenz plot 150, representing the first series 172 of four sensed R-waves (three RRIs).

The next series 174 of three RRIs provides the next ($\delta RR_i$, $\delta RR_{i-1}$) point 156 having a negative x-coordinate (the last RRI of series 174 being less than the immediately preceding RRI) and a positive y-coordinate (the middle RRI of series 174 being longer than the first RRI of series). This process of plotting ($\delta RR_i$, $\delta RR_{i-1}$) points continues with the three cycle series 176 providing data point 158 and so on.

Figure 5:
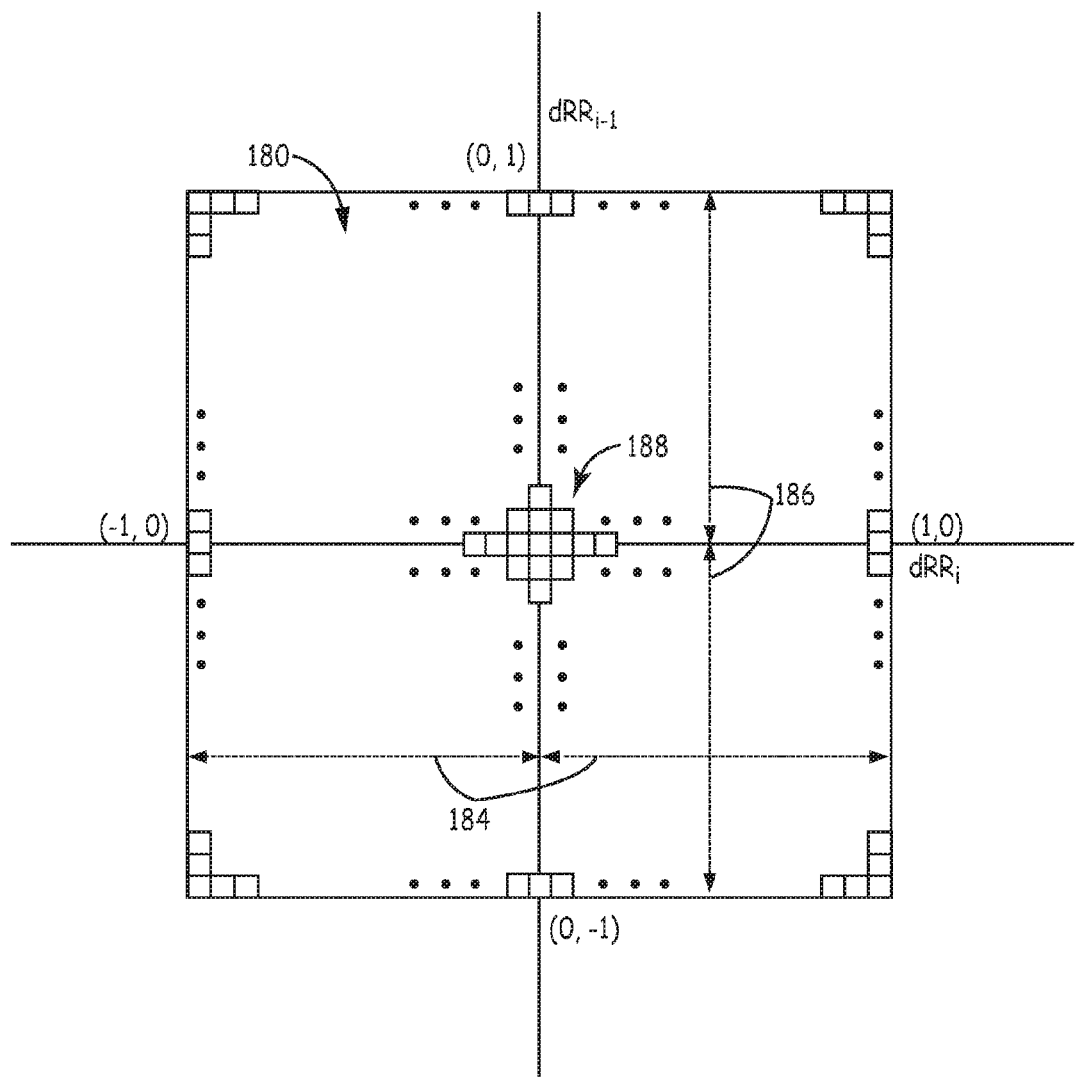
FIG. 5 is a diagram of a two-dimensional histogram representing a Lorenz plot area for detecting cardiac arrhythmias.

FIG. 5 is a diagram of a two-dimensional histogram representing a Lorenz plot area 150 for detecting cardiac arrhythmias. Generally, the Lorenz plot area 150 shown in FIG. 4 is numerically represented by a two-dimensional histogram 180 having predefined ranges 184 and 186 in both positive and negative directions for the $\delta RR_i$ coordinates (corresponding to x-axis) and $\delta RR_{i-1}$ coordinates (corresponding to y-axis), respectively. The two-dimensional histogram 180 is divided into bins 188 each having a predefined range of $\delta RR_i$ and $\delta RR_{i-1}$ values. In one example, the histogram range might extend from −1200 ms to +1200 ms for both $\delta RR_i$ and $\delta RR_{i-1}$ values, and the histogram range may be divided into bins extending for a range of 7.5 ms in each of the two dimensions resulting in a 160 bin×160 bin histogram 180. The successive RRI differences determined over a detection time interval are used to populate the histogram 180. Each bin stores a count of the number of ($\delta RR_i$, $\delta RR_{i-1}$) data points falling into each respective bin range. The bin counts may then be used by microprocessor 224 in determining RRI variability metrics and patterns for detecting a cardiac rhythm type.

An RRI variability metric is determined from the histogram bin counts. Generally, the more histogram bins that are occupied, i.e. the more sparse the distribution of ($\delta RR_i$, $\delta RR_{i-1}$) points, the more irregular the VCL is during the data acquisition time period. As such, one metric of the RRI variability that can be used for detecting AF, which is associated with highly irregular VCL may take into account the number of histogram bins that have a count of at least one, which is referred to as an "occupied" bin. In one example, an RRI variability metric for detecting AF, referred to as an AF score is determined by microprocessor 224 as generally described in the above-incorporated '911 patent. Briefly, the AF score may be defined by the equation:

AF Evidence=Irregularity Evidence−Origin Count−PAC Evidence wherein Irregularity Evidence is the number of occupied histogram bins outside a Zero Segment 188 defined around the origin of the Lorenz plot area. During normal sinus rhythm or highly organized atrial tachycardia, nearly all points will fall into the Zero Segment 188 because of relatively small, consistent differences between consecutive RRIs. A high number of occupied histogram bins outside the Zero segment 188 is therefore positive evidence for AF.

The Origin Count is the number of points in the Zero Segment 188 defined around the Lorenz plot origin. A high Origin Count indicates regular RRIs, a negative indicator of AF, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with premature atrial contractions (PACs) that occur at regular coupling intervals and present regular patterns of RRIs, e.g. associated with bigeminy (short-short-long RRIs) or trigeminy (short-short-short-long RRIs). In other embodiments, the AF score and/or other RRI variability score for classifying an atrial rhythm may be determined by microprocessor 224 as described in any of the above-incorporated '765, '316, '911, '569 and '368 patents.

The AF score is compared to an AF threshold for detecting AF based on the RRI analysis. The AF threshold may be selected and optimized based on historical clinical data of selected patient populations or historical individual patient data, and the optimal threshold setting may vary from patient to patient. If the metric crosses a detection threshold, the time period over which the RRIs were collected is classified as an AF segment. An AF detection is made when a threshold number of time periods are classified as AF, e.g., a single n-second or n-minute time period classified as AF based on the AF score meeting the AF threshold may result in an AF detection. In other examples, a higher number of time periods may be required to be classified as being AF before detecting the heart rhythm as AF.

The microprocessor 224 provides a response to the AF detection, which may include withholding or adjusting a therapy (e.g., withholding ATP or shock therapy for treating a ventricular tachyarrhythmia), storing cardiac signal data that can be later retrieved by a clinician, triggering patient notification system 250, transmitting data via telemetry circuit 330 to alert a clinician, and/or triggering other signal acquisition or analysis.

The RRI analysis may continue to be performed by microprocessor 224 after an AF detection is made to fill the histogram during the next n-second detection time interval. After each detection time interval, the AF score may be re-determined and the histogram bins are re-initialized to zero for the next detection time interval. The new AF score (or other RRI variability metrics) determined at the end of each detection time interval may be used to determine if the AF episode is sustained or terminated after the initial AF detection is made.

Figure 6:
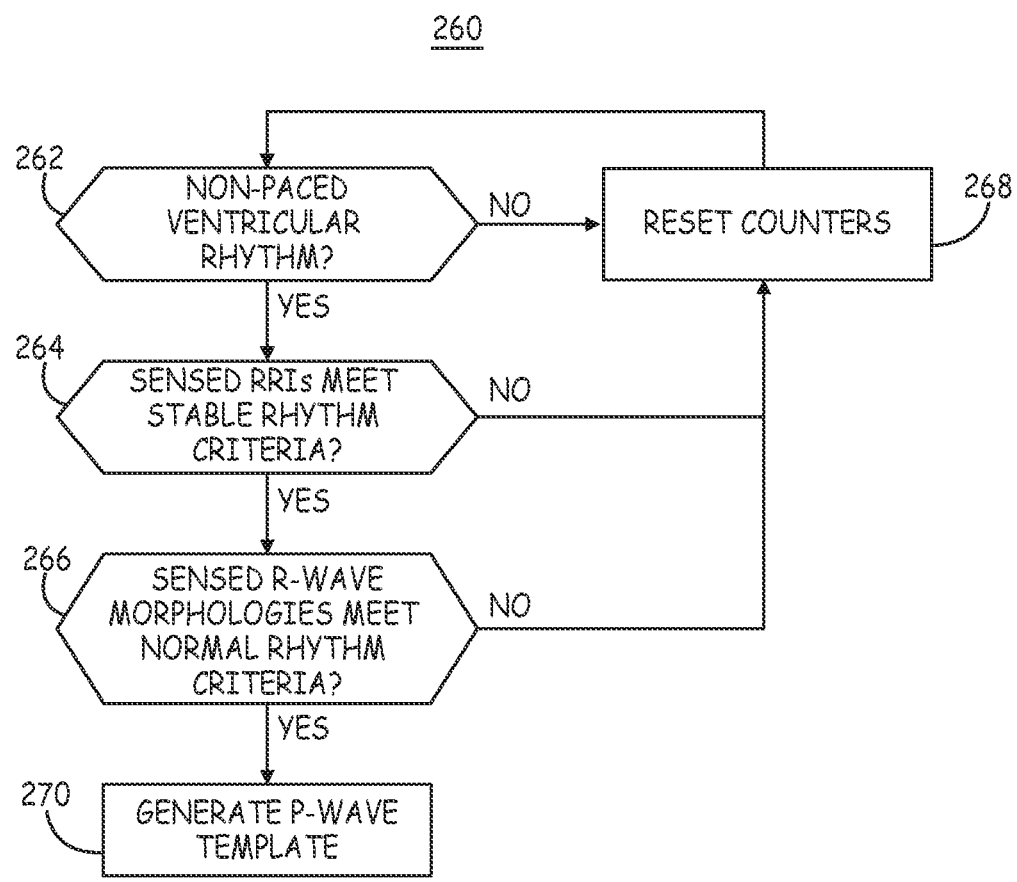
FIG. 6 is a flow chart of a method for analyzing the ventricular signals by the ICD of FIG. 1 or the ICD of FIGS. 3A and 3B prior to enabling P-wave template generation according to one example.

FIG. 6 is a flowchart 260 of a method for analyzing the ventricular signals by ICD 10 (or ICD 110) prior to enabling P-wave template generation according to one example. Flow charts presented herein are intended to illustrate the functional operation of the ICD or other therapy delivery or cardiac rhythm monitoring device, and should not be construed as reflective of a specific form of software, firmware or hardware necessary to practice the invention. It is believed that the particular form of software will be determined primarily by the particular system architecture employed in the device and by the particular detection and therapy delivery methodologies employed by the device. Providing software, firmware and/or hardware to accomplish the disclosed techniques in the context of any modern medical device, given the disclosure herein, is within the abilities of one of skill in the art.

Methods described in conjunction with flow charts presented herein may be implemented in a non-transitory computer-readable medium that includes instructions for causing a programmable processor to carry out the methods described, such as microprocessor 224. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

As illustrated in FIG. 6, prior to generating a P-wave template, microprocessor 224 verifies a normal, stable ventricular rhythm during which P-waves will be obtained for generating the P-wave template as described in FIG. 7 below. In one example, microprocessor 224 verifies that ventricular pacing is not occurring, block 262. A user may initiate the generation of the P-wave template at the time of ICD implant or during a patient follow-up. The user may visually verify that the ventricular rhythm is not a ventricular arrhythmia (VF or VT). For fully automatic P-wave template generation, ventricular rate during a non-paced rhythm may be required to be slow (e.g., less than 100 beats per minutes) so that the P-wave template) is not generated during a tachycardia. During an AF detection process, P-wave template matching may be performed in the presence of ventricular pacing when the rhythm is unknown. The generation of the P-wave template, however, may be performed when ventricular pacing is known not be present.

In the case of ICD 10, microprocessor 224 may confirm that pacer timing and control circuit 212 is not currently being controlled to deliver pacing pulses, e.g., for a predetermined number of consecutive RRIs or for at least a threshold number of RRIs out of a predetermined number of consecutive RRIs. In the case of ICD system 100, when an intra-cardiac pacemaker is present, such as pacemaker 101 (FIG. 3A), ICD 110 may detect pacing pulses being delivered by pacemaker 101. Pacing pulses may be detected from the cardiac electrical signal received by ventricular sense amplifier 200 or from a digital signal from A/D converter 222 (FIG. 2) via electrodes carried by lead 116. Techniques for detecting pacing pulses are generally disclosed in U.S. Pat. No. 4,226,245 (Bennett) and U.S. Pat. Publication No. 2015/0305642 (Reinke, et al.), both of which are incorporated herein by reference in their entirety.

Microprocessor 224 determines if the RRIs meet stable rhythm criteria at block 264. For example, microprocessor 224 may determine RRIs from a cardiac electrical signal received from A/D converter 222 or from R-wave sensed event signals received from ventricular sense amplifier 200. An RRI is identified by microprocessor 224 as being a normal ventricular interval if it is greater than a predetermined normal interval threshold, such 600 milliseconds or 700 milliseconds (ms). The stable rhythm criteria may further require a predetermined number of RRIs being identified as being normal. For example, at least four RRIs being greater than 600 ms may be required at block 264 for microprocessor 224 to confirm a stable rhythm. The stable rhythm criteria may require that the predetermined number of normal RRIs be consecutive in some examples. In other examples, non-consecutive intervals may be acceptable for satisfying the stable rhythm criteria. If ventricular pacing (or short RRIs) arise during the identification of the predetermined number of normal RRIs, the process may be restarted by resetting RRI counters at Block 268 and returning to Block 262.

Microprocessor 224 may determine if the morphology of the R-waves defining the RRIs that satisfy the stable rhythm criteria meet normal rhythm criteria, block 266. The R-wave morphology for each of the R-waves defining the predetermined number of normal RRIs may be compared to a morphology template or R-wave morphology features and required to match within a predetermined morphology matching threshold in order for the normal rhythm criteria to be satisfied, block 266. The morphology match may be determined using a waveform matching scheme used in cardiac signal analysis, such as a wavelet transform analysis scheme, or other morphology matching scheme. Examples of cardiac signal template acquisition and signal analysis methods are generally disclosed in U.S. Pat. No. 6,393,316 (Gillberg, et al.), U.S. Pat. No. 7,062,315 (Koyrakh, et al.), and U.S. Pat. No. 7,996,070 (van Dam et al.), each of which is incorporated herein by reference in their entireties.

According to one example, microprocessor 224 may determine whether at least four R-waves (or all five) associated with four identified normal RRIs each have an individual predetermined morphology match score that identifies the R-wave as having a normal, intrinsic R-wave morphology. If one or more of the R-waves do not meet the predetermined morphology match score identifying the R-wave as having the desired R-wave morphology, the process of identifying the predetermined number of R-waves is repeated by returning to block 268 to reset RRI and R-wave counters to generate a new predetermined number of RRIs meeting the stable rhythm criteria, blocks 262 and 264. The morphology matching requirements for meeting the normal rhythm criteria is reapplied, block 266, for the newly-acquired R-waves associated with the normal RRIs.

Once the predetermined number of normal RRIs defined by R-waves with the desired R-wave morphology are identified by the method illustrated by flow chart 260, P-wave template generation is enabled, block 270.

Figure 7:
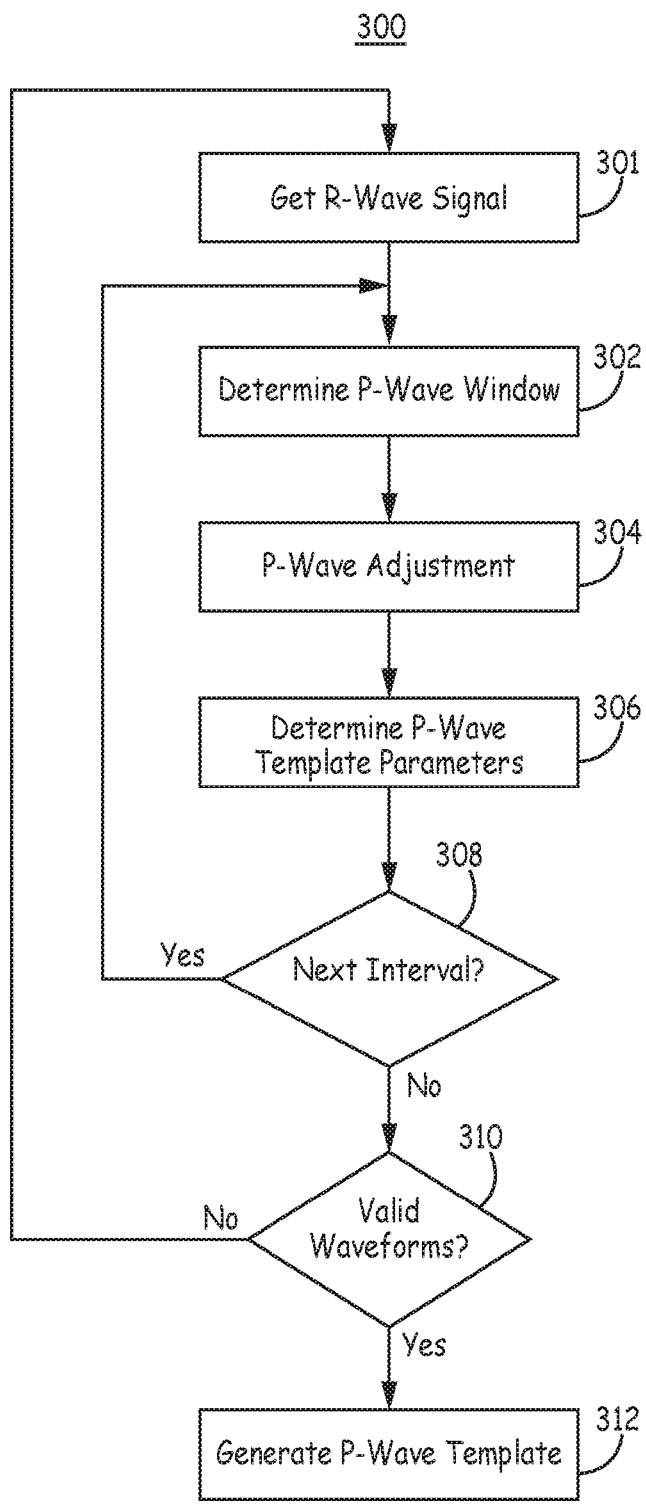
FIG. 7 is a flow chart of a method for generating a P-wave template according to one example.

FIG. 7 is a flow chart 300 of a method for generating a P-wave template by ICD 10 (or ICD 110) according to one example. The P-wave template is used by microprocessor 224 in classifying a time interval of a cardiac signal as AF (or non-AF) as described below. The process of flow chart 300 is enabled at Block 270 of FIG. 6.

Processor 224 identifies a predetermined number of normal R-waves, i.e., R-waves associated with non-paced, slow rhythms, having a desired R-wave morphology, block 301. The predetermined number of normal R-waves identified at block 301 may be the normal R-waves that were identified to satisfy the normal rhythm criteria at block 266 of FIG. 6. In other examples, normal R-waves may be identified after the normal rhythm criteria are met, using the same or similar criteria to the stable rhythm criteria and normal rhythm criteria described above in conjunction with flow chart 260.

The predetermined number of normal R-waves occurring at RRIs that are longer than a slow rhythm requirement, e.g., longer than at least 600 ms or longer than at least 700 ms, may be either consecutive or non-consecutive R-waves. The cardiac cycles associated with these R-waves are then used to generate the P-wave template, as described below in detail.

Microprocessor 224 determines a P-wave window for each of the predetermined number of normal R-waves, block 302. The P-wave window is used to identify a P-wave associated with each normal R-wave, as further described below in conjunction with FIGS. 8A and 8B. Upon identification of the P-wave using the P-wave window, the microprocessor 224 performs a P-wave adjustment for each identified P-wave, block 304, and determines P-wave template parameters associated with each P-wave, block 306, as will be described in detail below. Once the P-waves associated with each of the R-waves have been identified, block 302, the P-wave adjustment has been made, block 304, and the P-wave template parameters have been determined, block 306, for each of the predetermined number of P-waves, "No" branch of block 308, the microprocessor 224 determines whether the P-waves are valid waveforms for P-wave template generation, block 310, using the determined P-wave template parameters, determined at block 306, as will be described in detail below. If any of the predetermined P-waves are determined not to be a valid template generation waveform, "No" branch of block 310, the process of identifying the predetermined number of normal R-waves, block 301, for identifying P-waves and performing the P-wave validation process, blocks 302-310, is repeated. If all of the predetermined P-waves are determined to be valid waveforms from P-wave template generation, "Yes" branch of block 310, the P-wave template is generated using the valid waveforms, block 312, as will be described in detail below.

Figure 8A:
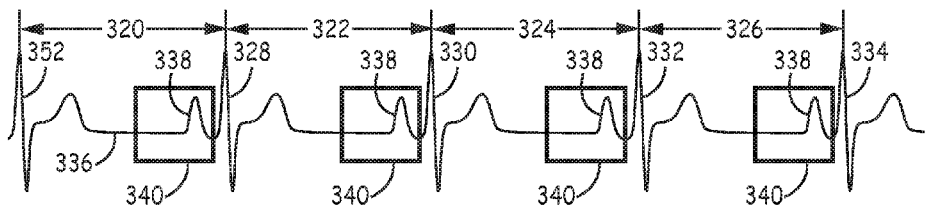
FIGS. 8A and 8B are schematic diagrams of identifying a P-wave window of a sensed cardiac signal according to one example.
Figure 8B:
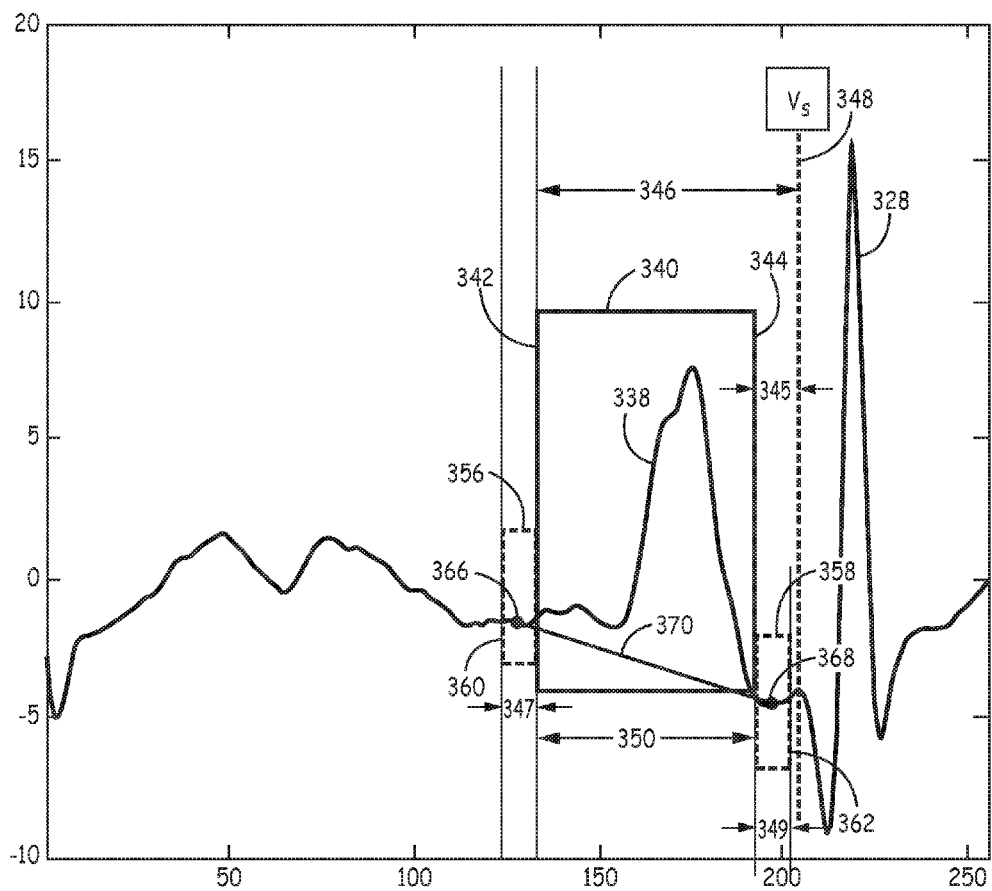

FIGS. 8A and 8B are schematic diagrams of identifying a P-wave window 340 of a sensed cardiac signal 336 acquired by ICD 10 or ICD 110 according to one example. As illustrated in FIG. 8A, the microprocessor 224 identifies four stable RR-intervals 320, 322, 324 and 326 associated with four sensed R-waves 328, 330, 332 and 334 of the sensed cardiac signal 336, and determines that the corresponding R-waves 328, 330, 332 and 334 each have the desired R-wave morphology, as described above in conjunction with FIG. 7. In order to identify a P-wave portion 338 of cardiac signal 336 preceding each of the predetermined number of R-waves 328, 330, 332 and 334, microprocessor determines a P-wave window 340 for each R-wave 328, 330, 332 and 334.

For example, as illustrated in FIG. 8B, in order to determine the P-wave window 340 associated with each R-wave 328, 330, 332 and 334, microprocessor 224 determines a P-wave window start point 342 and a P-wave window end point 344 preceding a respective sensed R-wave 328, 330, 332 or 334. For example, the P-wave window start point 342 is determined to be located a predetermined time interval 346 prior to a Vs event 348 associated with the R-wave 328 of the cardiac signal 336, and the corresponding P-wave window 340 is determined to extend a predetermined P-wave width 350, such as 242 ms, from the P-wave window start point 342, to P-wave end point 344 for example.

For R-wave template matching performed in the method described in conjunction with FIG. 7 and for P-wave template generation and matching, a far-field cardiac electrical signal having a relatively high P-wave amplitude may be chosen, e.g., using a sensing vector from the RV coil electrode 24 to housing 15 or between the SVC coil electrode 26 to RV coil electrode 24 (FIG. 1). In the example shown, in FIG. 8B, ventricular sensing by sense amplifier 200 of ICD 10 may be performed using a near-field ventricular signal, obtained from a true-bipolar sensing electrode vector (e.g., using RV tip electrode 28 and RV ring electrode 30) or an integrated bipolar sensing electrode vector (e.g., RV tip electrode 28 to RV coil electrode 24) for example. The Vs event 348 may be produced by sense amplifier 200 in response to a filtered, rectified near-field ventricular signal crossing a sensing threshold. As a result, the Vs event 348 shown in FIG. 8B may appear earlier than the R-wave 328 appearing on a far-field cardiac electrical signal, e.g., obtained from RV coil electrode 24 to SVC coil electrode 26, or between a lead-based electrode and housing 15. The relative timing of the Vs event 348 to the R-wave 328 may depend on the sensing electrode vector used to sense Vs event 348 and the sensing electrode vector used to sense the cardiac electrical signal used to generate the P-wave template. The P-wave window 340 may be set based on the Vs event 348 and the time interval 346 may be set taking into account any time delays between the Vs event 348 and the R-wave 328 of the cardiac signal that is used to sense P-waves.

Figure 9:
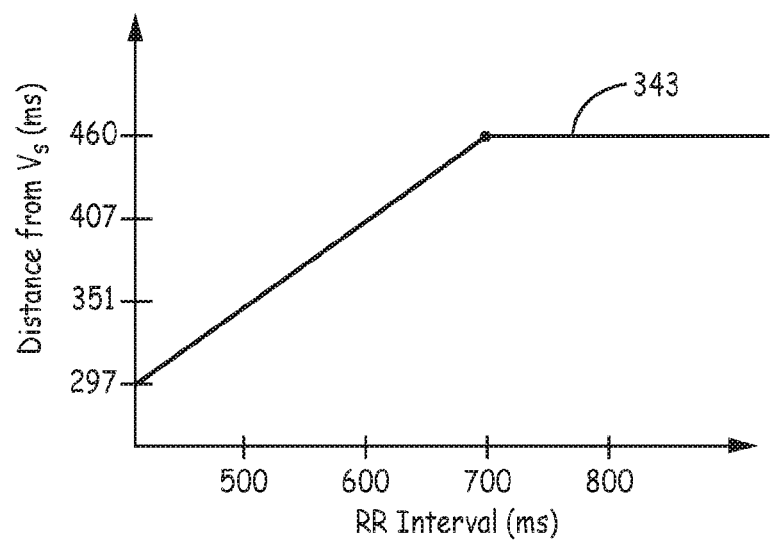
FIG. 9 is a graphical representation of determining a P-wave window start point based on a sensed R-wave according to one example.

FIG. 9 is a graphical representation of determining a P-wave window start point 342 (of FIG. 8B) based on a sensed R-wave by ICD 10 (or ICD 110) according to one example. This method for determining a P-wave window may be applied by microprocessor 224 both for obtaining P-waves used for P-wave template generation during a non-paced, slow ventricular rhythm and for iteratively obtaining a group of a predetermined number of P-waves during slow or fast ventricular rhythms, paced or non-paced, for use in confirming an RRI-based AF detection. With continued reference to FIG. 8B, the P-wave window start point 342 relative to the Vs event 348 may be dependent upon the heart rate associated with the Vs event 348, e.g., depending on RRI 320 (FIG. 8A). For example, for R-wave 328, the microprocessor 224 determines RRI 320 between R-wave 328 and an immediately preceding R-wave 352. Microprocessor 224 sets the starting point 342 of the P-wave window 340 based on the result.

In particular, according to one example, if RRI 320 is greater than an RRI baseline threshold, e.g., 700 ms, the predetermined time interval 346 from P-wave window start point 342 to Vs event 348 is set as a baseline time interval 343 of 460 ms. Since RRIs 320, 322, 324, and 326 may be verified as slow beats that are greater than the threshold RRI, the P-wave window start point 342 may be set to the baseline time interval of 460 ms for all P-waves being identified for use during P-wave template generation.

If the RRI is not greater than the RRI baseline threshold of 700 ms, the predetermined time interval 346 may be reduced from the baseline interval 343 by an amount relative to the determined RRI. For example, according to one example, the reduction in the time interval 346 may be determined from the graph illustrated in FIG. 9, so that if the RRI 320 is 600 ms, the time interval 346 is reduced from 460 ms to 406 ms. In some examples, RRIs used to set P-wave windows for generating a P-wave template are required to be at least 600 ms. As such, the time interval 346 may be set to be from 406 ms (when the RRI is 600 ms long) to 460 ms (when the RRI is 700 ms or longer) depending on the RRI length during P-wave template generation.

During AF detection, RRIs may be long or short. If the RRI 320 is 500 ms, the time interval 346 is reduced to 350 ms; and if the RRI 320 is 400 ms, the time interval 346 is reduced to 296 ms, and so forth. According to one example, the time interval 345 that the P-wave window end point 344 is located in time relative to the Vs event 348 remains the same regardless of the time of start point 342.

For example, the time interval 345 between the P-wave window end point 344 and the Vs event 348 may be set based on the time interval 346 that is utilized when the RRI 320 between R-wave 328 and a previous R-wave 352 is greater than the predetermined RRI threshold, 460 ms in the above example. Time interval 345 may be set as being approximately equal to 218 ms (460 ms–less the P-wave window width 350 which is set to 242 ms in this example). In this way, as the magnitude of the RRI decreases, the width 350 of the P-wave window 340 is reduced since the time interval 346 is reduced but time interval 345 remains fixed.

In the example shown in FIG. 9, the time interval 346 from a Vs event 348 to start point 342 of P-wave window 340 decreases linearly with RRI. In other examples, a non-linear relationship between time interval 346 and RRI may be defined, such as a step-wise change or other relationship.

As can been seen in FIG. 8B, in some instances the P-wave 338 may be shaped such that a beginning portion of the P-wave 338 along the cardiac signal 336 is located at a baseline amplitude that differs from the baseline amplitude of an ending portion of the P-wave 338, a phenomenon known as baseline wander. In order to account for this baseline wander, the microprocessor 242 may be configured to determine a first baseline wander window 356 associated with the beginning portion of the P-wave 338 and a second baseline wander window 358 associated with the ending portion of the P-wave 338.

For example, according to one example, illustrated in FIG. 8B, the ICD 10 or ICD 110 may determine that baseline wander windows 356 and 358 occur outside of the P-wave window 340, with the first baseline wander window 356 extending between the P-wave window start point 342 and a baseline window start point 360 located a predetermined time interval 347 prior to the P-wave window start point 342, such as 30 ms, for example, and the second baseline wander window 358 extending between the P-wave window end point 344 and a baseline window endpoint 362 located a predetermined time interval 349 from the P-wave window end point 344, such as 30 ms, for example.

Microprocessor 224 then determines both a first baseline end point 366 located within the first baseline wander window 356, and a second baseline end point 368 located within the second baseline wander window 358 based on the cardiac signal 336 within the respective windows 356 and 358. For example, endpoint 366 may be determined to be the average amplitude of the cardiac signal 336 within window 356, and endpoint 368 may be determined as being the average amplitude of the cardiac signal 336 within window 358. A linear P-wave baseline 370 extending between baseline end point 366 and baseline end point 368 may have a non-zero slope. An adjusted P-wave baseline may be determined by microprocessor 224 to extend between endpoint 366 and endpoint 368 to correct for baseline wander.

Figure 10A:
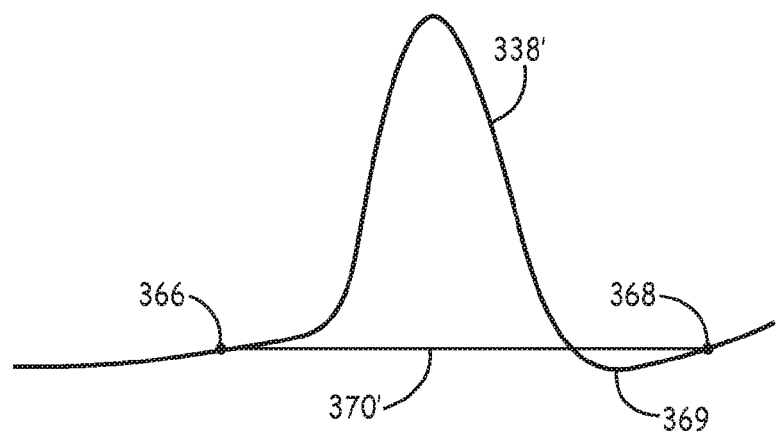
FIGS. 10A and 10B are schematic diagrams of a method for determining P-wave template parameters according to one example.
Figure 10B:
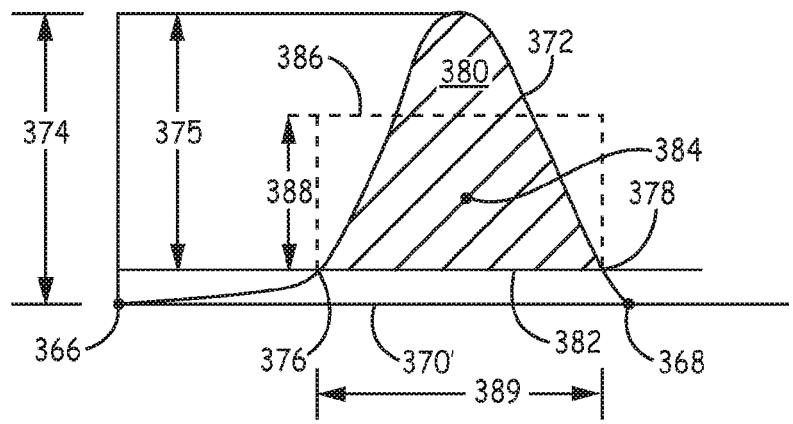

FIGS. 10A and 10B are schematic diagrams of a method for determining a baseline corrected, modified P-wave 372 from which P-wave template parameters may be determined by ICD 10 (or ICD 110) according to one example. As shown in FIG. 10A, the P-wave 338 is linearly adjusted according to the slope of the P-wave baseline 370 to provide a baseline adjusted P-wave 338' having a flat P-wave baseline 370'. The linear adjustment of the P-wave 338 is made by adjusting each sample point of P-wave 338 by the slope of the baseline 370, resulting in a baseline adjusted P-wave 338' having approximately zero slope of the adjusted P-wave baseline 370' between endpoints 366 and 368.

As shown in FIG. 10B, in some examples microprocessor 224 determines a modified P-wave 372 by determining if an absolute value of a maximum peak amplitude of the baseline adjusted P-wave 338' is greater than or equal to an absolute value of a minimum peak amplitude. If the absolute value of the maximum amplitude is greater than or equal to the absolute minimum amplitude, a maximum peak amplitude 374 of the modified P-wave 372 is set equal to the absolute maximum amplitude, and the negative portion 369 of the baseline adjusted P-wave 338', i.e., any negative P-wave signal sample point occurring during P-wave window 340, is set equal to zero to obtain modified P-wave 372 for use in generating a P-wave template.

On the other hand, if the absolute value of the maximum peak amplitude of adjusted P-wave 338' is not greater than or equal to the absolute value of the minimum peak amplitude, the maximum amplitude 374 of the modified P-wave 372 is set equal to the absolute minimum peak amplitude (and all negative sample points are rectified), and any positive portion of the baseline adjusted P-wave 338', i.e., any positive sample point of adjusted P-wave 338' during P-wave window 340, is set equal to zero to obtain the modified P-wave 372.

Microprocessor 224 may determine various parameters from the modified P-wave 372 as shown in FIG. 10B for verifying that the waveform is a valid P-wave and, if verified, for use in generating a P-wave template. Microprocessor 224 determines a first minimum amplitude point 376 located along a first side of the modified P-wave 372 and a second minimum amplitude point 378 located along a second side of the modified P-wave 372 opposite the first side (i.e., after the maximum peak having amplitude 374). According to one example, the first minimum amplitude point 376 and the second minimum amplitude point 378 may be determined based on the maximum amplitude 374 extending from the adjusted baseline 370' to the maximum peak of modified P-wave 372. For example, microprocessor 224 determines the first and second minimum points 376 and 378 as being located along the modified P-wave 372 at a portion of the maximum amplitude 374, such as one sixteenth of the maximum amplitude 374 or another percentage or portion of maximum amplitude 374.

Microprocessor 224 then determines the center of area 384 of P-wave area 380. The P-wave area 380 (indicated by diagonal lines) is defined by the modified P-wave 372 and modified baseline 382 extending between first minimum amplitude point 376 and second minimum amplitude point 378. P-wave area 380 has an amplitude 375 extending from the modified baseline 382 to the peak of the modified P-wave 372. In order to subsequently align the current four (or other selected number of) modified P-waves 372 for P-wave template generation, the microprocessor 224 determines a center of area 384 of each of the modified P-waves 372. According to one example, in order to approximate the center of area 384 of P-wave area 380, microprocessor 224 determines a P-wave center window 386 that is a rectangular estimation of the P-wave area 380 and is centered on the P-wave center of area 384. The P-wave area 380 may be determined, for example by summing all sample point amplitudes occurring along modified P-wave 372 between the first and second minimum amplitude points 376 and 378. The amplitude 388 of P-wave center window 386 may be determined as the P-wave area 380 normalized by the width 389 of the modified baseline 382 between points 376 and 378. P-wave center window 386 thus has a width 389 and a height 388 determined by normalizing the P-wave area 380 by the width 389. P-wave center window 386 has an area (the product of amplitude 388 and width 389) approximating P-wave area 380 and centered on center of area 384. The amplitude of the base of the P-wave center window 386 may correspond to the amplitude of points 376 and 378 such that height 388 of P-wave center window 386 (also referred to herein as P-wave center window amplitude 388) extends from the modified baseline 382. The position of center of area 384 in the y-direction (amplitude) may be determined as half of height 388. The position of center of area 384 in the x-direction (along modified baseline 382) is the midway point of width 389. The position of center of area 384 may be used for aligning multiple modified P-waves 372 for determining a P-wave template.

The determination of modified P-wave 372 by the linear adjustment for baseline wander correction, zeroing of sample points having opposite polarity of the maximum absolute value peak amplitude of P-wave 338, and setting a modified baseline 382 based on minimum amplitude points 376 and 378 is performed for each P-wave 338 of the determined R-waves 328, 330, 332 and 334. Determination of the approximate center of area 384 using a normalized P-wave center window 386 is performed for each modified P-wave 372. The centers of area 384 for each respective modified P-wave 372 are subsequently utilized to align a predetermined number of modified P-waves 372 for generating a P-wave template used to confirm a detected AF event, as described below, when all other P-wave template generation criteria are satisfied.

In response to AF detection based on RRIs, groups of a predetermined number of P-waves, e.g., four P-waves, may be obtained using the techniques shown in FIGS. 8B through 10B. The P-wave center window 386 may be determined for each of the P-waves in the group for determining P-wave parameters. P-wave template matching criteria may be applied to the P-wave parameters for confirming or not confirming the RRI-based AF as described below in conjunction with FIGS. 13A and 13B. Thus the techniques of determining a modified P-wave 370 and determining P-wave parameters based on the P-wave center window 386 may be performed during a confirmed slow rhythm for generating a P-wave template and during an RRI-based AF detection for use in a comparative analysis performed to confirm (or not confirm) the detected AF.

Figure 11:
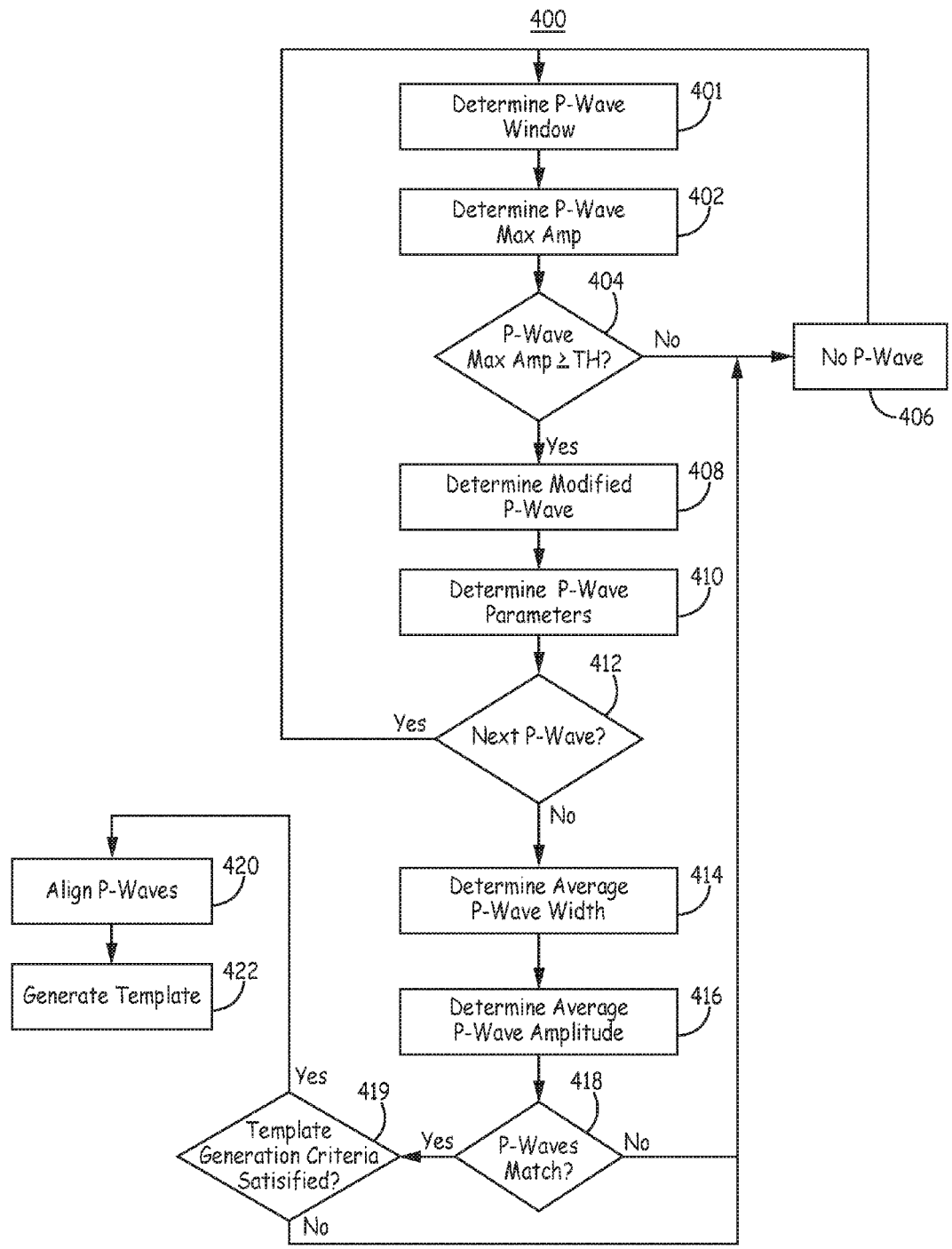
FIG. 11 is a flow chart of a method for generating a P-wave template for use in detecting AF according to one example.

FIG. 11 is a flow chart 401 of a method for generating a P-wave template for use in detecting AF by ICD 10 or 110 according to one example. As illustrated in FIG. 11, during generation of a P-wave template, the ICD 10 or 110 senses four R-waves 328, 330, 332 or 334 and identifies four corresponding P-waves 338, as described above. For each P-wave 338, the microprocessor 224 determines the P-wave window 340, at block 401, as described above in conjunction with FIG. 8B, and determines whether a maximum amplitude of the P-wave located within the window 340, at block 402, is greater than an amplitude threshold at block 404. Additionally or alternatively, microprocessor 224 may determine if a minimum magnitude change occurs within P-wave window 340 between a minimum sample point amplitude and a maximum sample point amplitude. For example, the magnitude change of cardiac signal 336 may be required to be at least twice a minimum peak amplitude identified within P-wave window 340. Other amplitude or magnitude change requirements may be applied at block 404 to ensure that the cardiac signal 336 within P-wave window 340 is likely a P-wave signal and not baseline noise fluctuation.

If the maximum amplitude is not greater than the maximum amplitude threshold or does not meet other amplitude or magnitude change criteria, "No" branch of block 404, the waveform is determined not to be a P-wave as indicated at block 406. The current four P-waves are discarded as a group, and the process is repeated by returning to block 401 to begin analysis of the next group of four determined P-waves.

If the maximum amplitude is greater than the maximum amplitude threshold and/or other maximum peak amplitude or magnitude change criteria are met, "Yes" branch of block 404, the microprocessor 224 determines the modified P-wave 372 for each of the four (or other predetermined number of) P-waves 338 as discussed above in conjunction with FIGS. 10A and 10B, at block 408. Microprocessor 224 determines P-wave parameters at block 410, such as the P-wave center window width 389 and P-wave center window amplitude 388, as described above in conjunction with FIG. 10B. When the determination of P-wave parameters of the modified P-wave 372 are determined for all four modified P-waves, "No" branch of block 412, microprocessor 224 determines average P-wave parameters from the four modified P-waves 372 at blocks 414 and 416.

Average P-wave parameters may include an average P-wave width and average P-wave amplitude. In one example, the average P-wave parameters are determined by microprocessor 224 utilizing the parameters determined for each modified P-wave 372 at block 410. For instance, the average P-wave width may be determined at block 414 as an average of all P-wave center window widths 389 determined for the modified P-waves. The average P-wave amplitude may be determined at block 416 as an average of all P-wave center window amplitudes 388 that were determined for the modified P-waves.

Microprocessor 224 then determines whether each of the modified P-waves 372 corresponding to the four original P-waves 338, match each other according to P-wave matching criteria applied at block 418. The P-wave matching criteria are applied to indicate the likelihood that the waveforms of all four modified P-waves are representative of true P-waves and acceptable for generating a P-wave template. One method for determining if the four modified P-waves match each other according to the P-wave matching criteria applied at block 418 is described next in conjunction with FIG. 12.

Figure 12:
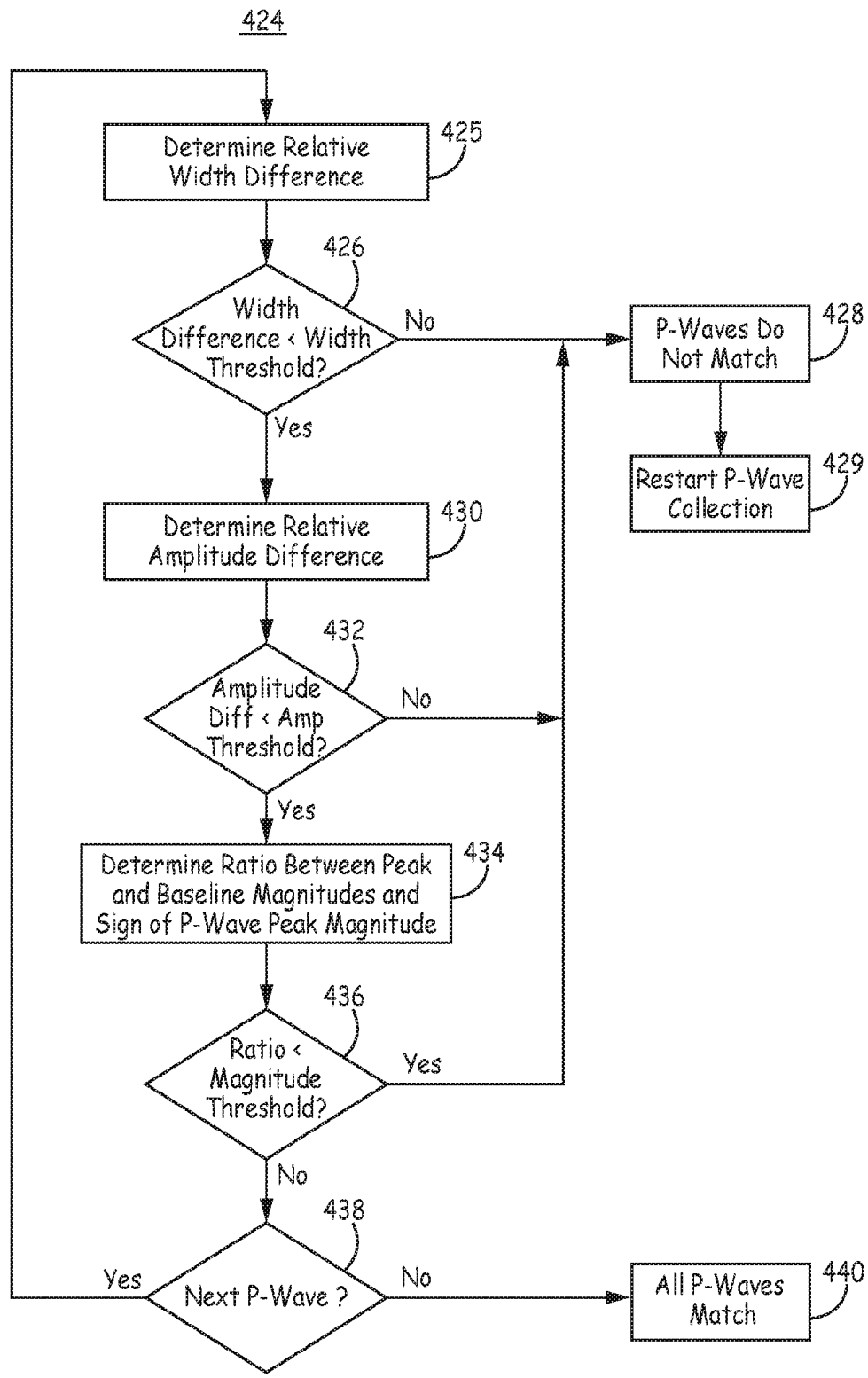
FIG. 12 is a flow chart of a method which may be performed by a medical device for determining P-wave matching according to one example of the techniques disclosed herein.

FIG. 12 is a flow chart 424 of a method which may be performed by ICD 10 or ICD 110 at block 418 of FIG. 11 for determining if the four (or other predetermined number of) modified P-waves 372 satisfy P-wave matching criteria according to one example. In order to make this determination as to whether the modified P-waves 372 match each other sufficiently to each be representative of a true P-wave and acceptable for use in generating a P-wave template, P-wave matching criteria are applied to each modified P-wave 372.

For each modified P-wave 372, microprocessor 224 determines a relative width difference, at block 425, by determining the absolute value of the difference between the P-wave center window width 389 determined for the modified P-wave 372 and the average P-wave width determined for the four modified P-waves (block 414 of FIG. 11). The relative width difference is compared to a width difference threshold, at block 426. If the width difference is not less than the width threshold, "No" branch of block 426, the waveform is determined not to be a P-wave at block 428. The four modified P-waves are deemed unreliable for generating a template. The four modified P-waves may be discarded. Microprocessor 224 returns to block 401 to obtain the next four R-waves and corresponding P-waves during new P-wave windows at block 429.

If the relative width difference is less than the width difference threshold for the current modified P-wave, "Yes" branch of block 426, microprocessor 224 determines a relative amplitude difference for the modified P-wave, at block 430, by determining the absolute value of the difference between the P-wave center window amplitude 388 of the modified P-wave 372 and the average P-wave amplitude determined for the current four modified P-waves (from block 416 of FIG. 11). The amplitude difference is compared to an amplitude difference threshold, at block 432, and if the amplitude difference is not less than the amplitude difference threshold, "No" branch of block 432, the waveform is determined not to be a P-wave at block 428. The next four R-waves and corresponding P-waves are determined at block 429 and the process returns to block 401 (FIG. 11), as described above, to be repeated using the next four P-waves.

If the relative amplitude difference is determined to be less than the amplitude difference threshold, "Yes" branch at block 432, microprocessor 224 may determine a magnitude change of the modified P-wave 372 by determining the difference between the modified baseline 382 (amplitude of points 376 and 378) and the maximum peak amplitude 375, block 434. The magnitude change is compared to a magnitude change threshold, block 436. If the ratio or difference between the peak amplitude 375 and modified baseline 382 is less than the magnitude change threshold, "Yes" branch of block 436, the waveform is determined not to be a P-wave, block 428. The next four R-waves and corresponding P-waves are determined, as described above, at block 429, and the process beginning at block 401 of FIG. 11 is repeated using the next four P-waves.

If the P-wave magnitude change is not less than the magnitude threshold, "No" branch of block 436, the current modified P-wave is determined to meet the P-wave matching criteria, and the process of flow chart 424 is repeated with the next modified P-wave until all four modified P-waves 372 corresponding to each one of P-waves 338 have been determined to satisfy the P-wave matching criteria, at block 440.

According to one example, the width threshold applied at block 426 and the amplitude threshold applied at block 432 are set equal to 62.5 percent. In other words, the width 389 of P-wave center window 386 is required to be within 37.5% of the average width determined for the four modified P-waves. The P-wave center window amplitude 388 of each of the modified P-waves 372 is required to be within 37.5% of the average amplitude determined the four modified P-waves.

The magnitude change threshold may be set as 50 percent in one example. In other words, the amplitude 382 of points 376 and 378 must be less than 50% of the peak amplitude 375 of a given modified P-wave 372 or the waveform is determined not to be a P-wave and all four modified P-waves are rejected for template generation. The magnitude change criterion is applied for verifying that each modified P-wave 372 is a true P-wave. In other examples, a magnitude change criterion applied to the modified P-wave 372 may be optional if the corresponding P-wave 338 or baseline adjusted P-wave 338' has already satisfied the maximum amplitude and/or magnitude change criteria applied at block 404 of FIG. 11 indicating that the waveform within P-wave window 340 is unlikely to be baseline noise fluctuations.

Other thresholds may be applied to each of the comparisons made at blocks 426, 430 and 438 and/or other P-wave parameters may be determined and compared to P-wave matching criteria to determine if the four modified P-waves 372 are each verified as P-waves and verified to match each other within acceptable limits or ranges for generating a P-wave template Returning to FIG. 11, if all four of the modified P-waves 372 are determined to satisfy the P-wave matching criteria using the process described in FIG. 12, "Yes" branch of block 418, microprocessor 224 may verify that other P-wave template generation criteria are met before producing a P-wave template using the four modified P-waves. Criteria may be applied to both the R-waves used to identify P-wave windows and the P-waves 338, baseline adjusted P-waves 338' and/or the modified P-waves 372. For example, each R-wave used to define a P-wave window may be required to have a morphology that matches each of the other R-waves or an R-wave template within a threshold morphology matching score range. In other examples, additional or alternative criteria applied to each modified P-wave in the process of flow chart 424 or applied at block 419 may include requiring the interval from point 376 to point 378 to be greater than a minimum threshold and less than a maximum threshold; requiring the average P-wave width determined from the four modified P-waves to be greater than a minimum threshold; and/or requiring the x- and/or y-position of the center of area 384 to fall within a predetermined range of the three other centers of area determined for the modified P-waves. Each individual center of area 384 may be required to have an x-coordinate position within a predetermined range of the average x-coordinate position.

Once all P-wave template generation criteria are satisfied at blocks 418 and 419, microprocessor 224 aligns the waveforms of three of the modified P-waves to the waveform of the fourth modified P-wave using the center of area 384 determined for each respective modified P-wave 372. For example, according to one example, the last three modified P-waves are aligned to the first modified P-wave by aligning the mid-points of the widths 389 of P-wave center windows 386. Microprocessor 224 determines an average waveform resulting from the aligned, modified P-waves, which is then set as the P-wave template, at block 422, for subsequent use in identifying P-waves during AF detection.

Figure 13A:
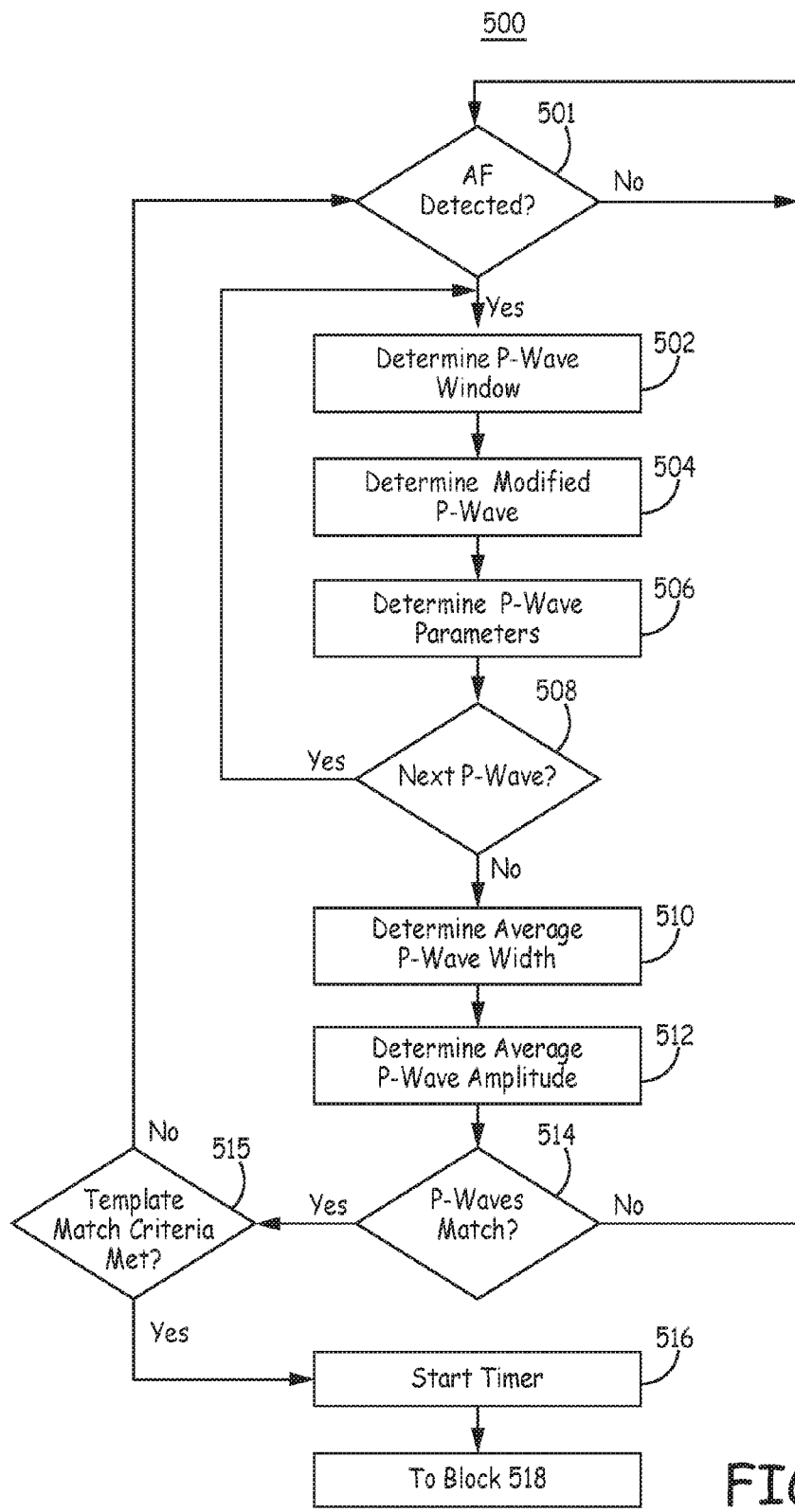
FIGS. 13A and 13B are a flow chart of a method for detecting an atrial arrhythmia by the ICD of FIG. 1 or the ICD of FIGS. 3A and 3B according to one example of the techniques disclosed herein.
Figure 13B:
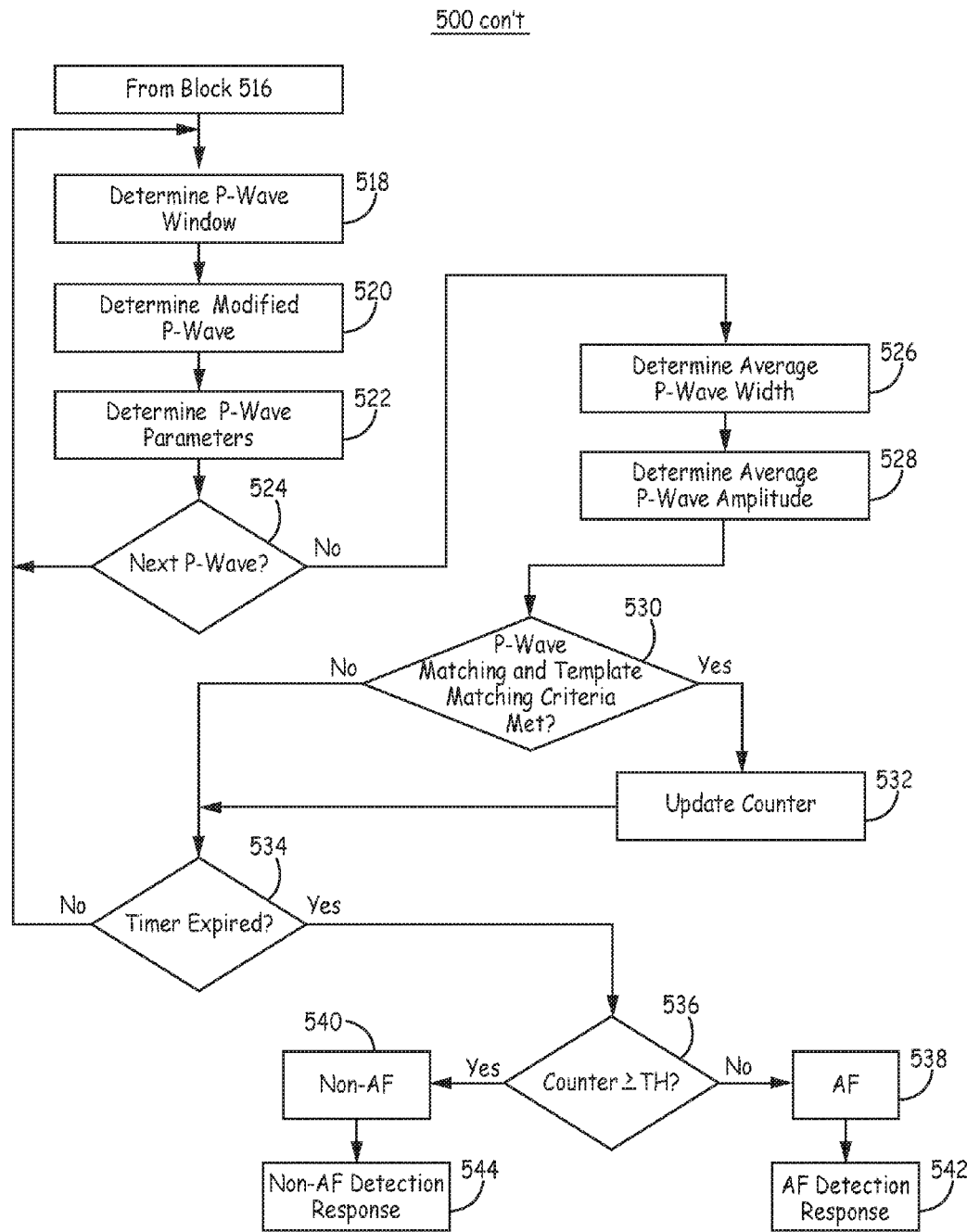

FIGS. 13A and 13B are a flow chart 500 of a method for detecting an atrial arrhythmia by ICD 10 or ICD 110 according to one example. As illustrated in FIGS. 13A and 13B, the ICD 10 (or ICD 110) identifies an AF event using an implemented AF detection scheme, such as the AF detection scheme described above in conjunction with FIGS. 4 and 5, based on RRI differences. As illustrated in FIG. 13A, upon detection of an AF event at block 500, microprocessor 224 identifies four R-waves associated with four RRIs. The four RRIs may be identified in the presence of ventricular pacing in some examples and may be fast or slow RRIs. In other words, an RRI threshold that is applied for obtaining P-waves for template generation may not be applied when obtaining P-waves for use in AF confirmation. Using the process described above in conjunction with FIGS. 8A and 8B, microprocessor 224 determines a P-wave window at block 502. A modified P-wave is determined at block 504, for each P-wave window, along with P-wave parameters at block 506, such as the P-wave center window width 389 and the P-wave center window amplitude 388 associated with the modified P-wave 372 as described in conjunction with FIG. 10B.

When the parameters have been determined for all four P-waves, "No" branch of block 508, microprocessor 224 utilizes the determined P-wave parameters to determine an average P-wave width at block 510, based on an average of the four P-wave center window widths, and an average P-wave amplitude at block 512, based on the average of the four P-wave center window amplitudes. A determination is then made for each of the modified P-waves as to whether each of the modified P-waves match each other according to P-wave matching criteria at block 514, which may include one or more thresholds applied to the individual P-wave parameters that are indicative of the likelihood that each of the waveforms is a P-wave.

According to one example, in order to make the determination as to whether a modified P-wave meets the P-wave matching criteria at block 514, the microprocessor 224 determines, in a manner similar to the scheme for generating a P-wave template described above, a corresponding relative width difference, a relative amplitude difference, and a P-wave magnitude change for each one of the four modified P-waves 372. In particular, in order to determine the width difference, microprocessor 224 determines the absolute value of the difference between the width 389 of P-wave center window 386 for each modified P-wave and the average width determined for the four modified P-waves. The width difference is then compared to a width threshold. To determine the amplitude difference, microprocessor 224 determines the absolute value of the difference between the P-wave center window amplitude 388 of the modified P-wave 372 and the average amplitude determined for the current four modified P-waves. This amplitude difference is compared to an amplitude threshold. Finally, in order to determine the magnitude change of the P-wave microprocessor 224 may determine the difference between modified baseline 382 and the maximum amplitude 375 for each of the modified P-waves, and compare the determined P-wave magnitude change to a magnitude change threshold.

If, for any one of the modified P-waves, either the width difference is not less than the width threshold, the amplitude difference is not less than the amplitude threshold, or the P-wave magnitude change is less than the magnitude threshold, the waveform is determined not to be a P-wave, and therefore all of the P-waves fail to meet the P-wave matching criteria, "No" branch at block 514. As a result, if the AF event continues to be detected based on other detection criteria, e.g., based on RRI difference analysis, "Yes" branch of block 501, microprocessor 224 determines the next four R-waves and corresponding P-waves, as described above, and the process of blocks 502-512 is repeated using the next four P-waves until four P-waves satisfying the P-wave matching criteria are obtained or until AF is no longer being detected at block 501 based on other AF detection criteria.

On the other hand if the width difference is less than the width threshold, the amplitude difference is less than the amplitude threshold, and the P-wave magnitude change is not less than the magnitude threshold for each of the adjusted P-waves, the P-waves are determined to satisfy the P-wave matching criteria at block 514. In some examples, the thresholds used to determine P-wave matching during AF detection are less stringent than the thresholds used to determine P-wave matching in the method of FIG. 12 during P-wave template generation. According to one example, during AF detection the width difference threshold and the amplitude difference threshold are set equal to 50 percent, and the magnitude change threshold is set to 50 percent. Each relative width difference and relative amplitude difference need only be within 50 percent of the average width and the average amplitude, respectively, rather than within 37.5 percent as required for P-wave template generation in the illustrative example given above.

Once the four modified P-waves are determined to match each other, the four modified P-waves are aligned using their respective centers of area 384 and an average of the four modified P-waves is determined and compared to the P-wave template at block 515. If the average of the four modified P-waves does not match the P-wave template, the process returns to block 501. Determination as to whether the average of the four modified P-waves matches the P-wave template may be based on comparisons between the P-wave center window width of the average of the four modified P-waves and the P-wave center window width of the P-wave template, between the P-wave center window amplitudes of the average of the four modified P-waves and the P-wave center window amplitude of the P-wave template, and a magnitude change of the average of the modified P-waves and a magnitude change of the P-wave template. The parameters compared for determining a P-wave template match may be analogous to the P-wave parameters used to determine if individual modified P-waves match each other, but with more stringent threshold requirements in some examples. In other examples, rather than determining an average of the four modified P-waves which is compared to the P-wave template, each of the four modified P-waves may be compared to the P-wave template at block 515 or averaged parameters from the four modified P-waves may be compared to analogous parameters of the P-wave template.

If the four modified P-waves are determined to match the P-wave template, "Yes" branch of block 515, microprocessor 224 sets a timer (or clock interval counter) at block 516 for analyzing P-wave signals for use in confirming the AF detection. The timer set at block 516 may be set to two minutes, though a longer or shorter interval may be used in other examples.

As Illustrated in FIG. 13B, when the timer is initiated, at block 516, the microprocessor 224 identifies the next group of four (or other predetermined number of) R-waves (or Vs events), and using the process described above, determines a P-wave window at block 518. A modified P-wave is determined from each P-wave window at block 520, and associated P-wave parameters are determined by microprocessor 224 at block 522 for each of the next group of four modified P-waves, such as the width 389 and the amplitude 388 of the P-wave center window 386.

When the P-wave parameters have been determined for the next four modified P-waves, "Yes" branch of block 524, microprocessor 224 utilizes the determined parameters to determine an average P-wave width at block 526 and average P-wave amplitude at block 528 for this next group of four modified P-waves. Microprocessor 224 determines if this next group of four modified P-waves match each other according to P-wave matching criteria and determines if the modified P-waves match the P-wave template according to template matching criteria at block 530, indicative of the likelihood that each of the waveforms are true P-waves.

The criteria applied at block 530 may be the same P-wave matching criteria applied at block 514 and the template matching criteria applied at block 515 in FIG. 13A. For example, the groups of four (or other predetermined number) modified P-waves are identified in an iterative procedure in which the four modified P-waves are compared to each other for determining whether P-wave matching criteria are met and compared to the P-wave template to determine whether template matching criteria are met at block 530. These comparisons are made using parameters determined from the four modified P-waves, such as the P-wave center window width 389, P-wave center window amplitude 388, x- and/or y-positions of center of area 384, or maximum amplitude 374. If the selected P-wave parameters of the group of modified P-waves match each other within predetermined matching thresholds, an average waveform of the group of modified P-waves may be determined by aligning the modified P-waves using center of area 384. Any combination of the parameters listed above may be determined from the average of the modified P-waves and compared to the analogous parameters of the P-wave template to determine that the group of modified P-waves matches the P-wave template and includes valid P-waves.

If the four modified P-waves are found to not satisfy the P-wave matching criteria or if the average of the four modified P-waves fail to satisfy the template matching criteria, "No" branch of block 530, and the time has not expired, the next group of P-waves is collected at block 518. In this way, groups of a predetermined number of P-waves are iteratively sensed and analyzed to identify valid P-waves during the RRI-based AF detection.

If P-wave matching criteria and template matching criteria are satisfied for the current group of modified P-waves being evaluated at block 530, microprocessor 224 increases a counter at block 532 to track the number of times the group of modified P-waves are determined to meet the P-wave matching criteria and the P-wave template matching criteria in response to all criteria being satisfied at block 530. The counter may be increased by one each time all four modified P-waves satisfy the template matching criteria or incremented once for each of the modified P-waves that were included in the group of modified P-waves used in the comparisons made at block 530.

When the counter has been updated, or the four P-waves are determined not to satisfy the P-wave matching criteria and the template matching criteria, "No" branch of block 530, microprocessor 224 determines whether the timer previous set at block 518 has expired, at block 534. If the timer has not expired, "No" branch of block 534, and if the AF event continues to be detected, "Yes" branch of block 501, the microprocessor 224 determines the next four R-waves and corresponding P-wave windows, as described above, and the process of blocks 518 through 530 for iteratively sensing and analyzing the next group of a predetermined number of P-waves is repeated as long as AF is still being detected according to the implemented AF detection algorithm, e.g., based on RRI differences.

If the timer has expired, "Yes" branch of block 534, microprocessor 224 determines whether the value of the counter being updated at block 532 has reached a count threshold at block 536. If the number of times that the iteratively sensed and analyzed groups of a predetermined number of P-waves match the P-wave template according to the criteria applied at block 530 is greater than or equal to the counter threshold before the timer expires, "Yes" branch of block 536, the event is determined to be a non-AF event. The RRI-based detection may be a false detection of AF. The presence of regularly occurring P-waves that satisfy P-wave template matching criteria contradicts the AF detection, e.g., made based on RRI differences analyzed using the Lorenz plot.

In response to detecting a non-AF rhythm, microprocessor 224 may control ICD 10 (or ICD 110) at block 544 to provide an appropriate response, which may include performing a function or combination of functions such as delivering a therapy, which may be a ventricular therapy; enabling a patient alarm; storing the detection of the non-AF rhythm within ICD memory with an indication that the rhythm was detected as AF based on the RRI analysis but not confirmed; and/or transmitting cardiac signal data associated with the non-AF rhythm detection.

If the number of times that the iteratively sensed and analyzed groups of P-waves match each other and the P-wave template during the given time period is not greater than or equal to a match threshold, "No" branch of block 536, the previous AF detection based on RRI differences (and/or other AF detection criteria) is confirmed; the time segment having fewer than the threshold number of P-waves matching the P-wave template is determined to be corroborating evidence of the RRI-based AF event detection as indicated at block 538.

In response to a confirmed AF detection, microprocessor 224 may control ICD 10 (or ICD 11) at block 542 to provide an AF detection response, which may include performing a function or combination of functions such as delivering an anti-atrial arrhythmia therapy; withholding a ventricular therapy; enabling a patient alarm; storing the detection of the AF event within ICD memory; and/or transmitting cardiac signal data associated with the AF detection. While not shown explicitly in FIG. 13B, it is to be understood that if a sufficient number of P-wave windows cannot be determined at block 518 before the timer expires at block 534, the counter will be determined to be less than the threshold at block 536 (perhaps without determining any P-wave parameters during the time interval), resulting in confirming an appropriate AF classification at block 538.

According to one example, during AF detection the P-wave template matching criteria applied at block 530 may include a width difference criterion, an amplitude difference criterion, a magnitude change criterion, and a polarity criterion. The width difference, amplitude difference, and polarity criteria are used to compare modified P-waves to analogous parameters of the P-wave template. For example, the width difference criterion may include comparing the relative width difference between the average P-wave center window width of a group of modified P-waves determined during AF to the P-wave center window width of the P-wave template to a threshold, which may be set equal to 62.5 percent in one example. The amplitude difference criterion may include comparing the relative amplitude difference between the average P-wave center window amplitude of a group of modified P-waves determined during AF to the P-wave center window amplitude of the P-wave template to a threshold, which may be set equal to 62.5 percent in one example. In other words, if each of the P-wave center window width and amplitude parameters determined from the average of the modified P-waves acquired during AF is within 37.5% of the analogous P-wave template width and amplitude parameters, the modified P-waves are determined to match the P-wave template. The polarity criterion may require that the polarity (positive or negative) of the maximum amplitude of the original P-waves 338 match the polarity of the P-waves used to generate the P-wave template. The template matching criteria may further include a modified P-wave magnitude change be within 50 percent of a magnitude change of the P-wave template. The timer set at block 516 may be set to two minutes, and the count threshold applied at block 536 may be set to two, for example, when groups of four modified P-waves are being analyzed at a time.

Figure 14:
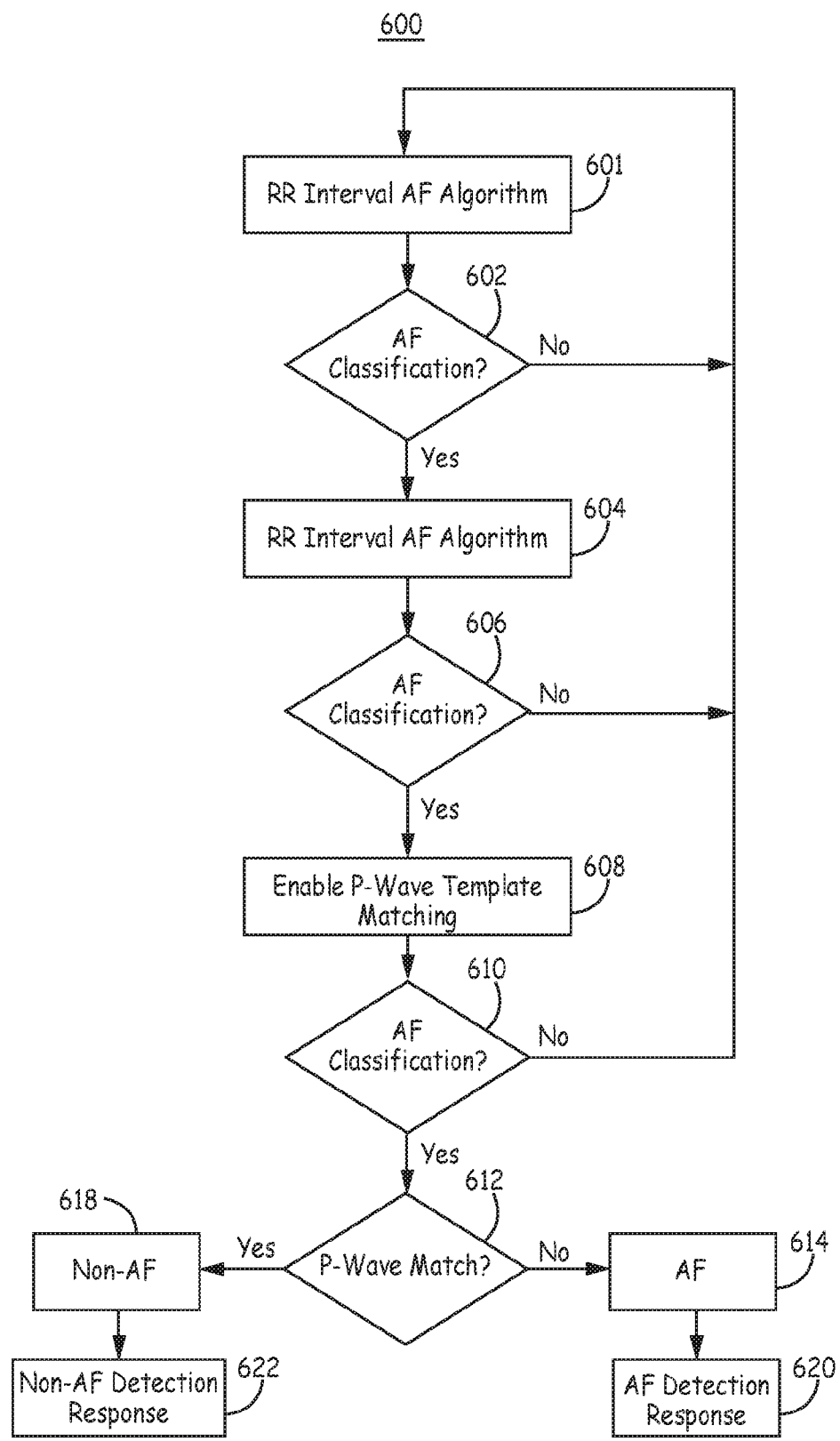
FIG. 14 is a flow chart of a method for detecting an atrial arrhythmia using the iterative P-wave signal analysis techniques disclosed herein according to one example.

FIG. 14 is a flow chart 600 of a method for detecting an atrial arrhythmia by ICD 10 or ICD 110 according to one example. As illustrated in FIG. 14, in order to detect AF, microprocessor 224 determines an AF score over a predetermined time period based on RRI differences at block 601 according to the RRI-based AF detection algorithm described above in conjunction with FIGS. 4 and 5. If one or more AF score(s) determined during a time period, e.g., a 2-minute time period, meet AF detection criteria at the expiration of the time period, the time period may be classified as AF. In other examples, other AF detection criteria may be required to be satisfied, in addition to or besides an RRI-based AF score, in order to classify the time period as AF at block 602.

According to one example, in order to enhance RRI-based AF detection specificity, if an AF classification is made at block 602, microprocessor 224 determines an AF score over the next n-minute time period at block 604. If the rhythm is classified as AF based on AF scores determined over two of the time periods, at blocks 602 and 604, "Yes" branch of block 606, microprocessor 224 enables P-wave template matching algorithm at block 612 to collect P-waves, determine modified P-waves, compare parameters of the adjusted P-waves to the previously generated P-wave template, and determined if P-wave template matching criteria are satisfied as described in conjunction with FIGS. 13A and 13B. In some examples, the RRI-based AF detection algorithm and the P-wave analysis are performed simultaneously during a third time period at block 610 and 612. If an AF score determined from RRI differences meets an AF detection threshold for the third time period, as determined at block 610, and the P-wave template matching criteria are satisfied during the third time period a threshold number of times based on an iterative analysis of groups of P-waves (as described in conjunction with FIG. 13B), determined at block 612, the cardiac rhythm is determined to be non-AF at block 618. The AF detection based on the AF classifications of the preceding two time periods (blocks 602 and 606) is overruled and not confirmed by the P-wave template matching analysis. The cardiac rhythm is detected as being a non-AF rhythm at block 618 or the AF detection is withheld until further signal analysis and/or additional time periods are analyzed. A response to the non-AF detection (or withholding of an AF detection) may be provided at block 622, which may include altering, withholding or delivering a therapy, storing cardiac signal data, enabling a patient alarm, transmitting an alarm signal remotely to a clinician, enabling or continuing cardiac rhythm detection algorithms until a positive rhythm detection can be made, or other appropriate response.

If AF is still being detected based on an AF score at block 610, and the P-wave analysis determines that P-wave template matching criteria are not met at least a threshold number of times during the time period, "No" branch of block 612, the AF detection is confirmed at block 614. A response to the AF detection may be provided at block 620, including withholding or altering a therapy, such as a ventricular therapy, storing data that can be later retrieved by a clinician, triggering an alarm to the patient or sent remotely to alert the clinician, delivering or adjusting a therapy, such as an atrial therapy, and/or triggering other signal acquisition or analysis.

It is understood that while the embodiment illustrated in FIG. 14 indicates detection of an AF event taking place over three separate two minute time periods, with the P-wave analysis being included within the third time period, at block 612, other examples could include one, two or more than two repeated AF detection analyses, and the P-wave analysis could be included with any one or combination of the AF determinations made using other cardiac signal analysis and AF detection criteria. It is also understood that the P-wave template may be generated upon receipt of a manual command during ICD implant or during an office visit. The template may be automatically updated (e.g., daily or weekly) by ICD 10 (or ICD 110) using the method of FIG. 11. Furthermore, the techniques disclosed herein may be implemented in any medical device utilizing a cardiac electrical signal, such as an intracardiac EGM, subcutaneous ECG or surface ECG vectors, including implanted or external cardiac rhythm monitoring devices, with or without therapy delivery capabilities.

Thus, an apparatus and method have been presented in the foregoing description for detecting and responding to atrial arrhythmia with reference to specific examples. It is appreciated that various modifications to the referenced examples may be made, including modifying the order of steps performed and/or modifying the combinations shown in the flow charts presented herein, without departing from the scope of the following claims.

The invention claimed is:

1. A method of detecting a cardiac event in a medical device, comprising:
   sensing a cardiac signal;
   identifying R-waves in the cardiac signal attendant ventricular depolarizations;
   determining RR-intervals between successive R-waves in the sensed cardiac signal;
   detecting an atrial tachyarrhythmia based on an analysis of the RR-intervals;

iteratively sensing groups of a predetermined number of P-waves attendant atrial depolarizations in response to detecting the atrial tachyarrhythmia; and confirming the atrial tachyarrhythmia based on an analysis of the iteratively sensed groups of P-waves.

2. The method of claim 1, wherein confirming the atrial tachyarrhythmia based on the analysis of the iteratively sensed groups of P-waves comprises:

determining P-wave parameters associated with each P-wave of the predetermined number of P-waves;

determining relative differences between the P-wave parameters;

determining whether each of the P-waves of the predetermined number of P-waves of an iteratively sensed group match each other based on the determined relative differences;

determining whether the predetermined number of P-waves of the iteratively sensed group match a P-wave template; and updating a counter in response to the iteratively sensed group of P-waves matching each other and matching the P-wave template, wherein the atrial tachyarrhythmia is confirmed in response to the counter remaining less than a counter threshold at expiration of a predetermined time period.

3. The method of claim 2, wherein determining relative differences between the P-wave parameters, comprises:

determining a relative width difference for each of the P-waves; and determining a relative amplitude difference for each of the P-waves.

4. The method of claim 2, further comprising:

determining the P-wave template prior to detecting the atrial tachyarrhythmia by sensing a second predetermined number of P-waves when a predetermined number of RR-intervals are greater than an interval threshold;

determining a baseline slope of each of the second predetermined number of P-waves;

adjusting each one of the second predetermined number of P-waves using the respective determined baseline slope, the adjusted P-wave having a zero baseline slope;

modifying each one of the adjusted P-waves by setting all points of the adjusted P-waves having an opposite polarity of a peak amplitude of the adjusted P-wave to zero;

determining a center of area of each of the modified P-waves;

aligning the centers of area of each of the modified P-waves; and generating a P-wave template from the aligned, modified P-waves.

5. The method of claim 1, wherein iteratively sensing the groups of the predetermined number of P-waves comprises:

determining P-wave windows based on the determined RR-intervals; and adjusting P-waves within the P-wave windows by determining a modified P-wave baseline.

6. The method of claim 2, further comprising:

determining a maximum amplitude of each of the P-waves;

determining, for each of the P-waves, a first minimum point and a second minimum point as a portion of the maximum amplitude;

determining an area of each of the P-waves based on a baseline extending between the first minimum baseline point and the second minimum baseline point;

determining a center of area window of each of the P-waves based on the area and a time interval extending between the first minimum point and the second minimum point; and determining the P-wave parameters from the center of area windows determined for each of the respective P-waves.

7. The method of claim 6, wherein determining the center of area window of each of the P-waves comprises:

determining an amplitude of the center of area window from the area and the time interval between the first minimum point and the second minimum point of the respective P-wave; and determining a width of the center of area window based on the time interval from the first minimum point and the second minimum point.

8. The method of claim 7, wherein determining the P-wave parameters, comprises:

determining a relative width difference based on the widths of the center of area windows determined for the P-waves; and determining a relative amplitude difference based on the amplitudes of the center of area windows determined for the P-waves.

9. The method of claim 1, wherein the atrial tachyarrhythmia is atrial fibrillation.

10. The method of claim 9, further comprising at least one of withholding a ventricular therapy and storing an episode of the cardiac signal in response to confirming the atrial tachyarrhythmia.

11. A medical device for detecting a cardiac event, comprising:

sensing circuitry configured to receive a cardiac signal from a plurality of electrodes coupled to the medical device; and a processor configured to:

identify R-waves in the cardiac signal attendant ventricular depolarizations;

determine RR-intervals between successive R-waves in the sensed cardiac signal, detect an atrial tachyarrhythmia based on an analysis of the RR-intervals; iteratively sense groups of a predetermined number of P-waves attendant atrial depolarizations in response to detecting the atrial tachyarrhythmia; and confirm the atrial tachyarrhythmia based on an analysis of the iteratively sensed groups of P-waves.

12. The medical device of claim 11, wherein the processor is configured to confirm the atrial tachyarrhythmia based on the analysis of the iteratively sensed groups of P-waves by:

determining P-wave parameters associated with each P-wave of the predetermined number of P-waves;

determining relative differences between the P-wave parameters;

determining whether each of the P-waves of the predetermined number of P-waves of an iteratively sensed group match each other based on the determined relative differences;

determining whether the predetermined number of P-waves of the iteratively sensed group match a P-wave template; and updating a counter in response to the iteratively sensed group of P-waves matching each other and matching the P-wave template, wherein the atrial tachyarrhythmia is confirmed in response to the counter remaining less than a counter threshold at expiration of a predetermined time period.

13. The medical device of claim 12, wherein the processor is configured to determine relative differences between the P-wave parameters by:
   determining a relative width difference for each of the P-waves; and
   determining a relative amplitude difference for each of the P-waves.

14. The medical device of claim 12, wherein the processor is further configured to:
   determine the P-wave template prior to detecting the atrial tachyarrhythmia by sensing a second predetermined number of P-waves when a predetermined number of RR-intervals are greater than an interval threshold;
   determine a baseline slope of each of the second predetermined number of P-waves;
   adjust each one of the second predetermined number of P-waves using the respective determined baseline slope, the adjusted P-wave having a zero baseline slope;
   modify each one of the adjusted P-waves by setting all points of the adjusted P-waves having an opposite polarity of a peak amplitude of the adjusted P-wave to zero;
   determine a center of area of each of the modified P-waves;
   align the centers of area of each of the modified P-waves; and
   generate a P-wave template from the aligned, modified P-waves.

15. The medical device of claim 11, wherein the processor is configured to iteratively sense the groups of the predetermined number of P-waves by:
   determining P-wave windows based on the determined RR-intervals; and
   adjusting P-waves within the P-wave windows by determining a modified P-wave baseline.

16. The medical device of claim 12, wherein the processor is further configured to:
   determine a maximum amplitude of each of the P-waves;
   determine, for each of the P-waves, a first minimum point and a second minimum point as a portion of the maximum amplitude;
   determine an area of each of the P-waves based on a baseline extending between the first minimum baseline point and the second minimum baseline point;
   determine a center of area window of each of the P-waves based on the area and a time interval extending between the first minimum point and the second minimum point; and
   determine the P-wave parameters from the center of area windows determined for each of the respective P-waves.

17. The medical device of claim 16, wherein the processor is configured to determine the center of area window of each of the P-waves by:
   determining an amplitude of the center of area window from the area and the time interval between the first minimum point and the second minimum point of the respective P-wave; and
   determining a width of the center of area window based on the time interval from the first minimum point and the second minimum point.

18. The medical device of claim 17, wherein the processor is further configured to determine the P-wave parameters, by:
   determining a relative width difference based on the widths of the center of area windows determined for the P-waves; and
   determining a relative amplitude difference based on the amplitudes of the center of area windows determined for the P-waves.

19. The medical device of claim 11, wherein the processor is configured to detect the atrial tachyarrhythmia as atrial fibrillation.

20. The medical device of claim 19, further comprising therapy output circuitry and a memory, wherein the processor is further configured to provide a response to confirming the atrial tachyarrhythmia, the response comprising at least one of controlling the therapy output circuitry to withhold a ventricular therapy and storing an episode of the cardiac signal in the memory.

21. The medical device of claim 11, wherein the plurality of electrodes are carried by an extra-cardiovascular lead.

22. A non-transitory, computer-readable storage medium storing instructions for causing a processor included in a medical device to perform a method for detecting a cardiac event, the method comprising:
   sensing a cardiac signal;
   identifying R-waves in the cardiac signal attendant ventricular depolarizations;
   determining RR-intervals between successive R-waves in response to the sensed cardiac signal;
   detecting an atrial tachyarrhythmia based on an analysis of the RR-intervals;
   iteratively sensing groups of a predetermined number of P-waves attendant atrial depolarizations in response to detecting the atrial tachyarrhythmia; and
   confirming the atrial tachyarrhythmia based on an analysis of the iteratively sensed groups of P-waves.

23. The medical device of claim 11, wherein the processor is configured to iteratively sense the groups of the predetermined number of P-waves by:
   setting a timer; and
   iteratively sensing the groups of the predetermined number of P-waves until the timer expires.

* * * * *